(12) United States Patent
Ammirati

(10) Patent No.: US 9,603,510 B2
(45) Date of Patent: Mar. 28, 2017

(54) METHOD AND APPARATUS FOR DELIVERING AN ENDOSCOPE VIA MICROSURGICAL INSTRUMENTS WHILE PERFORMING MICROSCOPIC SURGERY

(76) Inventor: Mario Ammirati, Columbus, OH (US)

( * ) Notice: Subject to any disclaimer, the term of this patent is extended or adjusted under 35 U.S.C. 154(b) by 1226 days.

(21) Appl. No.: 13/474,610

(22) Filed: May 17, 2012

(65) Prior Publication Data

US 2012/0296217 A1 Nov. 22, 2012

Related U.S. Application Data

(60) Provisional application No. 61/487,058, filed on May 17, 2011.

(51) Int. Cl.

| A61B 1/00 | (2006.01) |
|---|---|
| A61B 1/06 | (2006.01) |
| A61B 1/04 | (2006.01) |
| A61B 90/00 | (2016.01) |
| A61B 1/313 | (2006.01) |
| A61B 90/20 | (2016.01) |

(52) U.S. Cl.
CPC .............. *A61B 1/04* (2013.01); *A61B 90/361* (2016.02); *A61B 1/0014* (2013.01); *A61B 1/0623* (2013.01); *A61B 1/3135* (2013.01); *A61B 90/20* (2016.02)

(58) Field of Classification Search
CPC .............. A61B 1/0014; A61B 1/00098; A61B 1/00174; A61B 1/00179; A61B 1/00183; A61B 17/00234; A61B 2017/00292; A61B 2017/00296; A61B 19/5223; A61B 19/5225; A61B 19/5227

USPC ....... 600/104, 109, 114, 153, 160, 162, 170, 600/171, 175, 182
See application file for complete search history.

(56) References Cited

U.S. PATENT DOCUMENTS

| 4,759,348 | A | 7/1988 | Cawood |
| 5,095,887 | A | 3/1992 | Leon et al. |
| 5,433,725 | A * | 7/1995 | Christian ............... A61B 17/29 600/104 |
| 5,601,549 | A | 2/1997 | Miyagi |
| 5,643,176 | A | 7/1997 | Persidsky |
| 5,667,473 | A | 9/1997 | Finn et al. |
| 5,857,961 | A | 1/1999 | Vanden Hoek et al. |
| 5,976,077 | A | 11/1999 | Wittens et al. |

(Continued)

*Primary Examiner* — Anhtuan T Nguyen
*Assistant Examiner* — William Chou
(74) *Attorney, Agent, or Firm* — The Belles Group, P.C.

(57) ABSTRACT

The present invention relates to a surgical apparatus that includes a surgical instrument including an elongated shaft extending along a longitudinal axis from a proximal end to a distal end, a working element coupled to the distal end of the elongated shaft for manipulating tissue; an endoscope having a tubular body including an image fiber, an endoscopic lens coupled to a distal end of the tubular body and operably coupled to the image fiber, the endoscopic lens defining a viewing field about a central axis; and the endoscope mounted to the elongated shaft of the surgical instrument, the endoscopic lens protruding from an outer longitudinal surface of the elongated shaft, the central axis of the viewing field being oblique to the longitudinal axis of the elongated shaft and intersecting the outer longitudinal surface, the working element located within the viewing field and separated from the central axis by a distance.

15 Claims, 19 Drawing Sheets

(56) References Cited

U.S. PATENT DOCUMENTS

| | | |
|---|---|---|
| 6,266,182 B1 | 7/2001 | Morita |
| 6,277,064 B1* | 8/2001 | Yoon .................. A61B 1/00177 600/104 |
| 6,432,041 B1* | 8/2002 | Taniguchi ............ A61B 1/0055 600/117 |
| 6,551,315 B2 | 4/2003 | Kortenbach et al. |
| 6,648,902 B2 | 11/2003 | Colgan et al. |
| 6,682,477 B2 | 1/2004 | Boebel et al. |
| 6,893,441 B2 | 5/2005 | Brommersma et al. |
| 7,050,225 B2 | 5/2006 | Nakamura |
| 7,087,010 B2* | 8/2006 | Ootawara .......... A61B 1/00098 600/104 |
| 7,615,002 B2 | 11/2009 | Rothweiler et al. |
| 7,927,271 B2 | 4/2011 | Dimitriou et al. |
| 2002/0072761 A1* | 6/2002 | Abrams et al. ........ A61B 17/00 606/190 |
| 2002/0111534 A1* | 8/2002 | Suzuki ............... A61B 1/00098 600/102 |
| 2004/0230097 A1 | 11/2004 | Stefanchik et al. |
| 2006/0111609 A1 | 5/2006 | Bacher |
| 2006/0247495 A1 | 11/2006 | Bacher et al. |
| 2007/0293719 A1 | 12/2007 | Scopton et al. |
| 2008/0021269 A1 | 1/2008 | Tinkham et al. |
| 2009/0054733 A1 | 2/2009 | Marescaux et al. |
| 2010/0016659 A1* | 1/2010 | Weitzner ............ A61B 1/00073 600/104 |
| 2010/0137681 A1 | 6/2010 | Ewers et al. |
| 2010/0245557 A1 | 9/2010 | Luley, III et al. |

* cited by examiner

METHOD AND APPARATUS FOR DELIVERING AN ENDOSCOPE VIA MICROSURGICAL INSTRUMENTS WHILE PERFORMING MICROSCOPIC SURGERY

CROSS-REFERENCE TO RELATED PATENT APPLICATIONS

The present application claims the benefit of U.S. Provisional Patent Application Ser. No. 61/487,058, filed May 17, 2011, the entirety of which is incorporated herein by reference.

FIELD OF THE INVENTION

The present invention relates to instruments and methods for minimally invasive microsurgical procedures and treatment of diseases using microscopic and endoscopic combination.

BACKGROUND OF THE INVENTION

Endoscopic surgery is performed by inserting the endoscope into a body cavity. The endoscopic image is displayed on its own monitor. The endoscope has its own carrier that may house other channels to accommodate surgical instruments, irrigation and suction. The endoscope provides wide angle view, the ability to look around the corner and enhanced illumination by bringing the light close to the target; all these features are desirable during surgical procedures. However, the main drawback of purely endoscopic surgery is the lack of 3-D viewing capability. In fact, many patient accidents during endoscopic procedures across all specialties are attributed to lack of a three-dimensional visualization. All these pluses and minuses apply to the use of the endoscope in all different types of surgeries including neurosurgical procedures. In the last 10-15 years there has been an increased use of the endoscope in neurosurgical procedures. If a neurosurgeon wants to use the endoscope, he/she must go through a course and learn a new surgical technique, the endoscopic technique.

Microscopic surgery, on the other side, is a technique generally known by all neurosurgeons and both spinal and intracranial neurosurgery is often performed with the aid of an operating microscope that allows great illumination and 3-D vision in a narrow operating space. Indeed there is virtually no hospital—small or big, community or academic—where neurosurgery is performed that does not have an operating microscope that gets upgraded or even changed every couple of years.

It would be desirable to be able to use the unique advantages of the endoscope and to combine them with established microsurgical techniques. A need exists to combine the beneficial uses of the endoscope to augment many microscopic neurosurgical procedures such as vascular, tumor and spinal procedures, yet no combination exists.

SUMMARY OF THE INVENTION

It is therefore an object of the invention to provide an endoscope/microscope combination that would make the heavily discussed controversy between proponent of the microscope and of the endoscope (see for example the heated controversy between proponents of endoscopic pituitary surgery versus proponents of microscopic pituitary surgery) obsolete and irrelevant. Such endoscope/microscope combination requires the development of a process/platform that would make this combination doable with minimal disruption to established microsurgical techniques.

This new platform has the potential to become what Laparoscopy represented for General Surgery, Ob-Gyn, and several other specialties in the early 1990's, namely a complete revolution not only for the doctors, but also for organizations that had the vision to invest and enter into the very beginning of this market.

Therefore, it is an object of the present invention to provide a process where about microsurgical instruments become the endoscope carriers.

Another object of the invention is the use of a device that allows the attachment of the endoscope to the microsurgical instrument.

It is still another object of the invention some dedicated micro-instruments specifically designed to accommodate the endoscope during microsurgical procedures.

In according with these objects, the embodiment of the present invention relies on the clipping/wrapping/attaching of the endoscope to the micro-surgical instrument and to the insertion of the endoscopic image into the oculars of the 3-D operating microscope space using off the shelf readily available technology that is packaged in many operating microscopes. This embodiment would make use of the endoscope more efficient by not crowding the surgical space with new tools but rather transforming each and every instrument used in microscopic neurosurgery into an endoscope carrier.

Besides, the addition of the bi-dimensional endoscope image into the tri-dimensional microscopic space would easily integrate the endoscope information into a familiar 3-D space, making the surgery inherently safer and more efficient. The neurosurgeon will see through the microscopic oculars both images: the endoscopic and microscopic ones.

The embodiment of the invention includes flexible endoscope with diameter no bigger then 3 mm, high definition image capacity, disposable or not, without or with light source, which is attached to the last 10 cm of micro surgical instrumentals.

This procedure is done through a clip or a "Velcro type" pad. The clips or pads may be disposable. The clips or pads may be snapped on the carrier micro-surgical instrument and on the endoscope at different points on the respective shafts so as to have multiple potential positions of the endoscope on the carrier micro-surgical instrument. This arrangement allows the endoscope to be used as an instrument and not as a new procedure tool. The surgeon may ask at several junctures of the operation: "load the endoscope on the suction, forceps, etc. and let me see what additional information I can get," and the assistant nurse will attach the endoscope to the micro-surgical instrument in order to attend the surgeon's needs.

The embodiment includes also the design of special instruments to allow the attachment of the endoscope when necessary.

In one embodiment the present invention can be a surgical apparatus comprising: a surgical instrument comprising an elongated shaft extending along a longitudinal axis from a proximal end to a distal end, a working element coupled to the distal end of the elongated shaft for manipulating tissue; an endoscope having a tubular body including an image fiber, an endoscopic lens coupled to a distal end of the tubular body and operably coupled to the image fiber, the endoscopic lens defining a viewing field about a central axis; and the endoscope mounted to the elongated shaft of the surgical instrument, the endoscopic lens protruding from an outer longitudinal surface of the elongated shaft, the central axis of the viewing field being oblique to the longitudinal axis of the elongated shaft and intersecting the outer longitudinal surface, the working element located within the viewing field and separated from the central axis by a distance.

In another embodiment the present invention can be a surgical apparatus comprising: a surgical instrument comprising an elongated shaft extending along a longitudinal axis from a proximal end to a distal end, a working element coupled to the distal end of the elongated shaft for manipulating tissue, the elongated shaft comprising a first indexing feature; an endoscope having a tubular body including an image fiber, an endoscopic lens coupled to a distal end of the tubular body and operably coupled to the image fiber, the endoscopic lens defining a viewing field about a central axis, the tubular body comprising a second indexing feature; and the endoscope mounted to the elongated shaft of the surgical instrument so that the first and second indexing features mate with one another so as to prevent relative rotation between the elongated shaft and the tubular body, the working element located within the viewing field.

In yet another embodiment the present invention can be a surgical system comprising: a surgical apparatus comprising: a surgical instrument comprising an elongated shaft and a working element coupled to a distal end of the elongated shaft for manipulating tissue; an endoscope having a tubular body including an image fiber, an endoscopic lens coupled to a distal end of the tubular body and operably coupled to the image fiber, the endoscopic lens defining a viewing field about a central axis; and the endoscope mounted to the elongated shaft of the surgical instrument so that the working element is located within the viewing field; a microscope comprising an ocular lens; and a display displaying an image perceived by the ocular lens and an image perceived by the endoscopic lens.

In even yet another embodiment the present invention can be a method of performing surgery comprising: mounting an endoscope to a micro-surgical instrument so that a working element of the micro-surgical instrument is located within a viewing field of the endoscope; positioning a microscope so that an ocular lens of the microscope perceives a surgical site; manipulating tissue within the surgical site using the working element of the micro-surgical instrument; and displaying, in a display, an image perceived by the endoscope and an image perceived by the ocular lens.

BRIEF DESCRIPTION OF THE DRAWINGS

The present invention will become more fully understood from the detailed description and the accompanying drawings, wherein.

DETAILED DESCRIPTION

Figure 1:
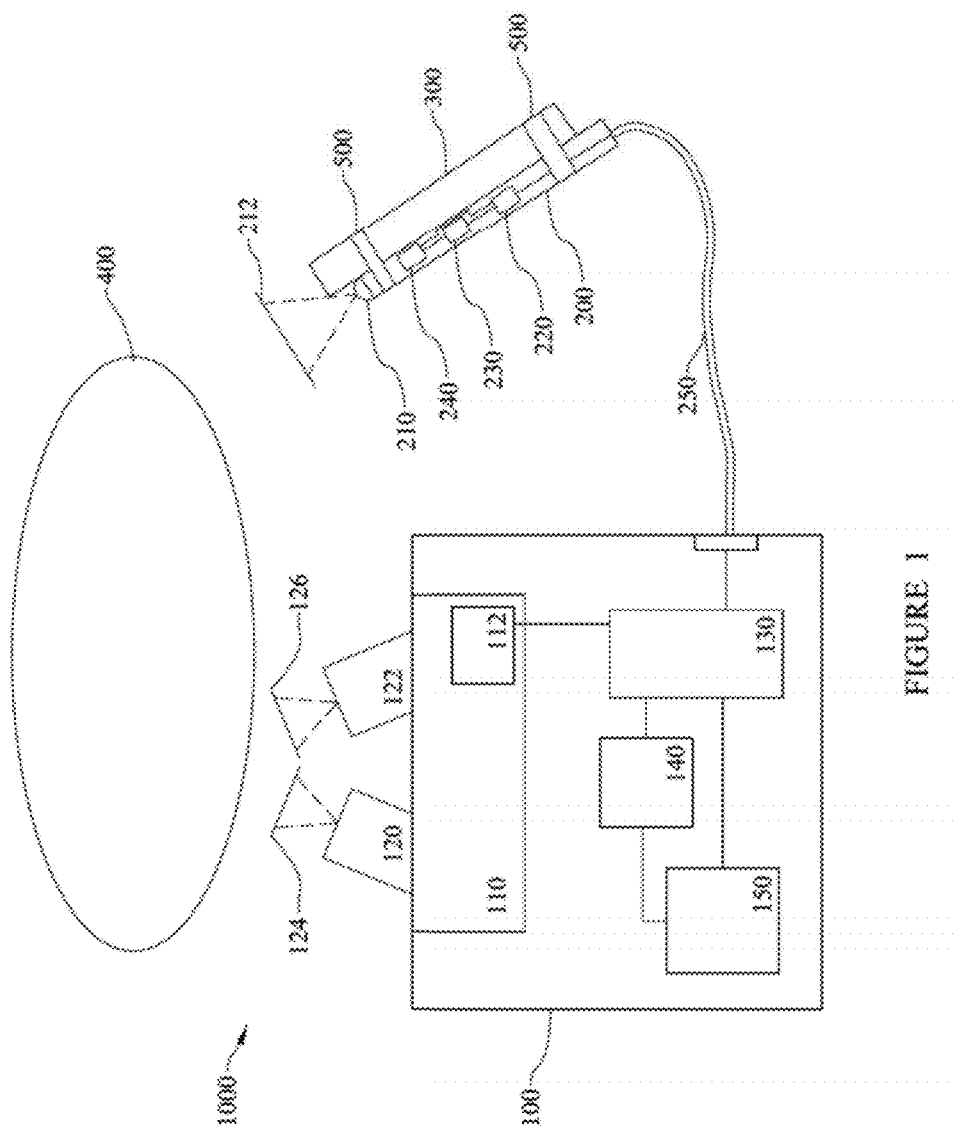
FIG. 1 is a schematic drawing of an endoscope/microscope combination assembly according to one embodiment of the present invention.

The following description of the preferred embodiment(s) is merely exemplary in nature and is in no way intended to limit the invention, its application, or uses.

The description of illustrative embodiments according to principles of the present invention is intended to be read in connection with the accompanying drawings, which are to be considered part of the entire written description. In the description of the exemplary embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "left," "right," "top," "bottom," "front" and "rear" as well as derivatives thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," "secured" and similar refer to a relationship wherein structures are secured or attached to one another either directly or indirectly through intervening structures, as well as both movable or rigid attachments or relationships, unless expressly described otherwise. Moreover, the features and benefits of the invention are described by reference to the exemplary embodiments illustrated herein. Accordingly, the invention expressly should not be limited to such exemplary embodiments, even if indicated as being preferred. The discussion herein describes and illustrates some possible non-limiting combinations of features that may exist alone or in other combinations of features. The scope of the invention is defined by the claims appended hereto.

Referring to FIG. 1, an endoscope/operating microscope assembly system 1000 according to one embodiment of the present invention is illustrated. The embodiment illustrated in FIG. 1 comprises an operating microscope assembly 100, an endoscope assembly 200, a surgical instrument 300, a surgical site 400, and at least one coupling mechanism 500. It should be noted that some of the elements of FIG. 1 are generically shown as blocks. This is done because, in its broadest sense, the invention is not limited to any particular structure, shape and/or arrangement for the endoscope/operating microscope assembly system 1000. Thus, it should be noted that those elements that are generically shown as blocks may take on a variety of other shapes and sizes in other embodiments of the present invention.

The operating microscope 100 comprises two optical lenses 120 and 122, an ocular viewing area 110, a processor/controller 130, a power source 140 and memory 150. As discussed in more detail below, the processor/controller 130 is configured to receive and process the image data from the endoscopic lens 210 of the endoscope assembly 200 and render an image in an endoscopic display 112 (depicted here in the ocular viewing area 110). The processor/controller 130 is also configured to transmit the image data from the endoscope assembly 200 to memory 150 for storage (temporary or permanent). The power source 140 is configured to provide power to at least the processor/controller 130, memory 150 and endoscopic display 112 (or endoscopic viewing area 112) of the operating microscope 100.

The optical lenses 120, 122 are configured to provide the user with an enhanced view of the surgical site 400. Collectively, the optical lenses 120, 122 may be referred to as "an ocular lens," whereas each of the optical lenses 120, 122 may be referred to as "an ocular." It should be noted that although the surgical site 400 is generically shown as a circle, the surgical site 400 can be any area of a mammalian organism, living or diseased, on which the user desires to perform surgery.

The orientation of the optical lenses 120, 122 and the location of focus of each lens may be adjusted by the user. Both optical lenses 120, 122 work in conjunction with the ocular viewing area 110 of the operating microscope 100 to provide the user with an enhanced view of the surgical site 400. In one embodiment, the optical lens 120 is configured to provide the user with an enhanced view of the surgical site 400 through the user's left eye along the first plane 124, while the optical lens 122 is configured to provide the user with an enhanced view of the surgical site 400 through the user's right eye along the second plane 126. Each optical lens 120, 122 provides the user with an enhanced two-dimensional view of the surgical site 400, while the two planes 124, 126 are non-coplanar. Therefore, the combination of the two optical lenses 120, 122 provide the user with an enhanced three-dimensional view of the surgical site 400.

As discussed in more detail below, the ocular viewing area 110 displays images perceived by the ocular lens 120, 122, while the endoscopic viewing area 112 displays images perceived by the endoscopic lens 210 of the endoscope 200. As illustrated in FIG. 1, in one embodiment the endoscopic viewing area 112 may be overlaid or displayed within the ocular viewing area 110, so that the user may view both the ocular viewing area 110 and endoscopic viewing area 112 simultaneously via the ocular lens 120, 122 of the microscope 100. In such embodiments, the endoscopic display 112 is a digital screen that may be overlaid in the ocular viewing area 110 over or adjacent to the image or view from the microscopic oculars 100, and provide the user with an additional two-dimensional, non-coplanar view of the surgical site 400. Further, in one embodiment of the present invention, the ocular viewing area and the endoscopic viewing area may be consecutively displayed on the display in response to a switching signal, the switching signal created by the processor/controller 130 in response to a user input. As discussed in more detail below, the present invention is not limited to the specific type or configuration of ocular viewing area 100 and endoscopic display 112. Further, the endoscopic display 112 is discussed in more detail below in conjunction with the endoscope assembly 200.

It should be noted that the present invention is not so limited, and that in alternate embodiments the ocular viewing area 110 may be just microscopic oculars (without the endoscopic display 112), be a combination of microscopic oculars and an external display showing an image perceived by the endoscopic lens 210 (e.g. an endoscopic image), or just an external display showing a plurality of images (e.g., images perceived from the ocular lens 120, 122 and images perceived by the endoscopic lens 210 of the endoscope 200). Further, in alternate embodiments of the present invention, the ocular viewing area 110 may be used to display images perceived by more than two components (e.g., microscopes and endoscopes) simultaneously. For example, a three-dimensional image from the ocular lens 120, 122 of the operating microscope 100 may be displayed simultaneously with more than one other two-dimensional image from more than one endoscope 200 captured from non-coplanar views. Therefore, the present invention is not limited to the use of one endoscope 200 in conjunction with the operating microscope 100, and thus more than one endoscopic display 112 may be presented to the user simultaneously along with the three-dimensional image provided by the operating microscope 100.

It should be noted that the ocular viewing area 110 of the present invention is not limited to the display of images from only an operating microscope 100 and/or endoscope assemblies 200, but that in alternate embodiments, the ocular viewing area 110 may display other image data, such as, for example MRI images, in conjunction with images from an operating microscope 100 and/or images from endoscope assemblies 200.

Further, it should be noted that in one embodiment of the present invention, the ocular viewing area 110 and the endoscopic viewing area 112 are both displayed on a display. The display may be internal to the microscope 100 and therefore, may be viewed by the user using the ocular lens 120, 122. However, in another embodiment, the display may be external to the microscope 100, such as an external display screen and therefore, may be viewed by the user without the need of the ocular lens 120, 122. In embodiments that comprise a display, the ocular viewing area and the endoscopic viewing area may be consecutively displayed on the display in response to a switching signal, the switching signal created by the processor/controller 130 in response to a user input.

The endoscope assembly 200 comprises an endoscopic lens 210, a processor/controller 220, memory 230, a power supply 240, and a communication link 250. As discussed in more detail below, the endoscope assembly 200 may be mounted to a surgical instrument 300 with one or more coupling mechanisms 500 to provide the user with an additional viewing angle of the surgical site 400 during operation. Although shown generically as a rectangle, it should be noted that the surgical instrument 300 may be any instrument used during surgery.

Figure 2:
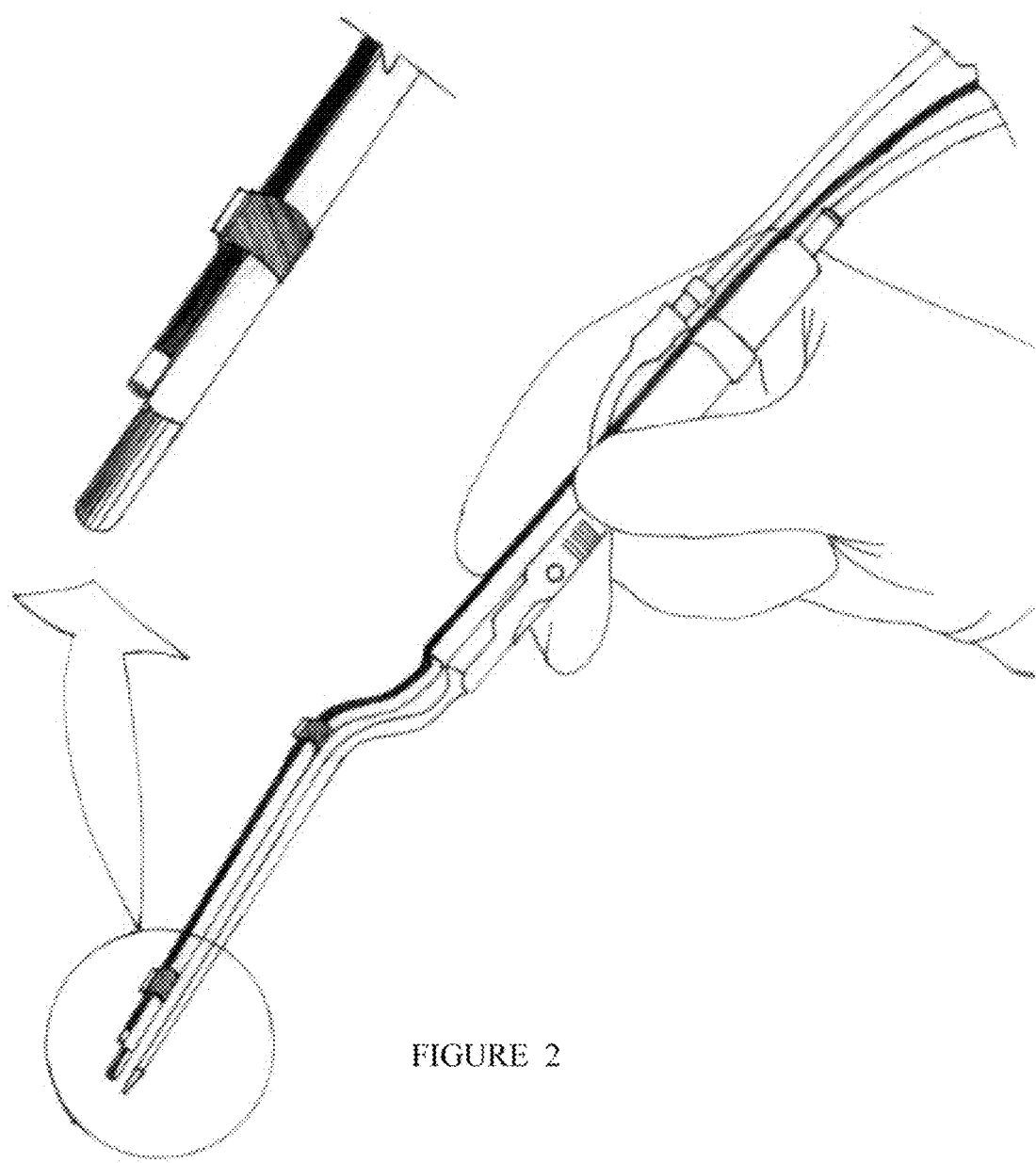
FIG. 2 is a perspective view of an endoscope incorporated with a surgical instrument according to one embodiment of the present invention.
Figure 3:
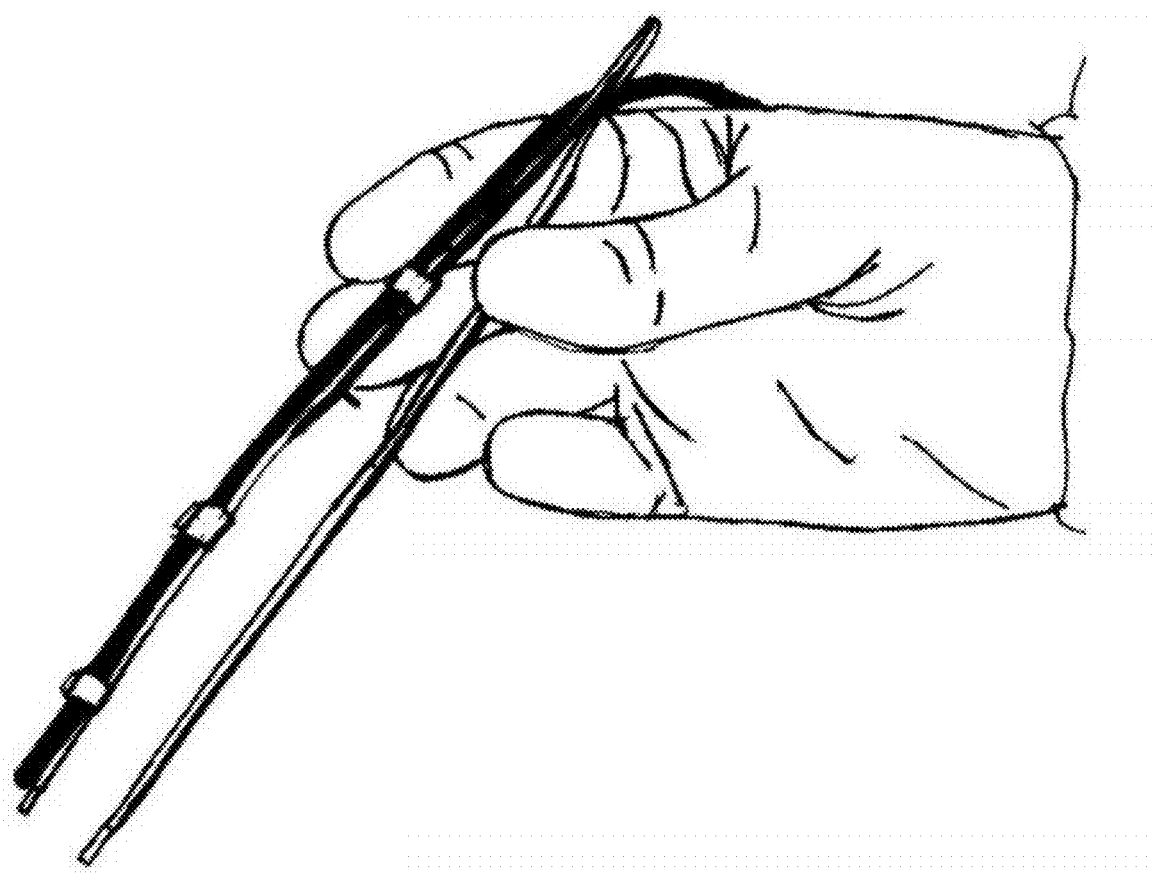
FIG. 3 is a perspective view of an endoscope incorporated with a surgical instrument using coupling mechanisms according to one embodiment of the present invention.
Figure 4:
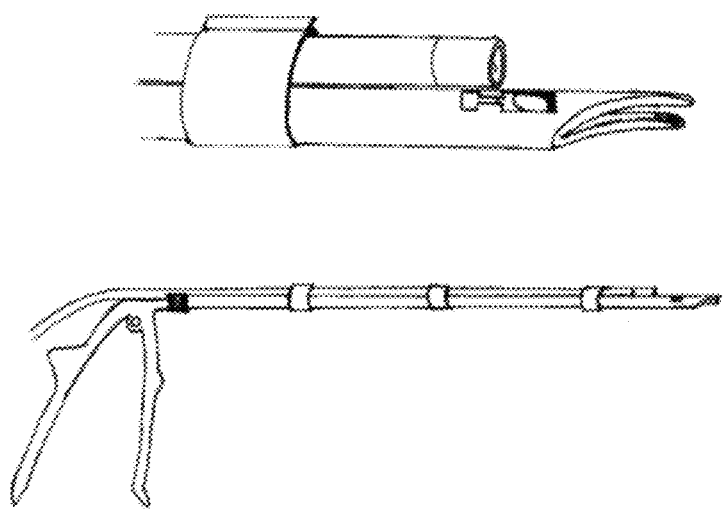
FIG. 4 is an exploded perspective view showing a distal portion of an endoscope incorporated with a surgical instrument and a coupling mechanism according to one embodiment of the present invention.

FIGS. 2-4 are perspective views of the endoscope incorporated with a surgical instrument according to embodiments of the present invention. It should be noted that FIGS. 2-4 are non-limiting examples of the use of the endoscope/surgical tool combination in according with the present invention.

As discussed in more detail below, in one embodiment of the present invention, the endoscope 200 comprises a tubular body comprising a proximal end, a distal end, and an image fiber, and an endoscopic lens 210. The endoscopic lens 210 is coupled to the distal end of the tubular body and operably coupled to the image fiber. In one embodiment of the present invention, the endoscopic lens 210 is an objective lens. As also discussed in more detail below, the endoscopic lens 210 defines a viewing field V-V about a central axis A-A.

In the preferred embodiment, the entire endoscope assembly 200 is flexible. The flexibility of the endoscope 200 enables the endoscope 200 to be easily and securely mounted to a plurality of different surgical instruments 300 having different shapes and sizes. The invention, however, is not so limited and in alternate embodiments parts or all of the endoscope assembly 200 may be rigid.

The processor/controller 220 is configured to receive and process the image data perceived by the endoscopic lens 210, and transmit the image data via the communication link 250 to the operating microscope 100 for display in the endoscopic display 112. The power supply 240 is configured to provide power to the ocular lens 210, the processor/controller 220, and the memory 230 of the endoscope 200. The memory 230 is configured to store the image data (either permanently or temporarily) captured by the ocular lens 210.

The endoscopic lens 210 of the endoscope 200 is configured to capture images of a surgical site 400 along the third plane 212. The third plane 212 is non-coplanar with the first and second planes 124, 126 of the ocular lenses 120, 122 of the operating microscope 100. Therefore, the endoscopic lens 210 provides the user with a third enhanced view of the surgical site 400 from another perspective to enhance operational experience. Specifically, in embodiments where the endoscope 200 is securely mounted to a surgical instrument 300, the endoscope 200 may provide the user with a third enhanced view of the surgical site from the location and perspective of the surgical instrument 300 being used. Therefore, as the surgical instrument 300 is moved, the third enhanced view taken from the endoscopic lens 210 of the endoscope 200 is constantly changing. Of course, depending on the positioning of the endoscope, the two views may be co-planar with one another.

As noted above, in one embodiment the ocular viewing area 210 is configured to simultaneously provide the user with an image of the surgical site 400 perceived by the ocular lens 120, 122 of the operating microscope 100 along with an image of the surgical site 400 perceived by the endoscopic lens 210 of the endoscope 200. In the preferred embodiment, the two views are non-coplanar and therefore provide the user with multiple views of the surgical site 400 from different perspectives. This enhances the user's ability to work with and manipulate the surgical site 400 they are viewing.

For example, in microscopic surgery, the present invention provides the user not only with the three-dimensional view of the surgical site 400 through the ocular viewing area 110 of the operating microscope 100, but also simultaneously provides the user with an additional, non-coplanar, two-dimensional view of the operating site 400 taken by the endoscope 200 (also through the ocular viewing area 110, and specifically in the endoscopic display 112). This enables the user to view the surgical site 400 from two different angles through one viewing area (the ocular viewing area 110). Further, if the endoscope is secured to a surgical instrument 300, then the user may perform traditional endoscope surgery with the aid of an additional, non-coplanar, three-dimensional view from the ocular lens 120, 122 of the operating microscope 100. This enhances the view angles the user has during a surgical procedure and provides for the combined benefits of endoscopic surgery and microscopic surgery in one method.

The user may simultaneously view images perceived from both the operating microscope 100 and the endoscope 200. As noted above, the images may be viewed by the user by looking through the ocular viewing area 110, or by using an external display. As the user moves the endoscope 200 around the surgical site 400, the user may continuously alter the view in the endoscopic display 112 while keeping the view from the operating microscope 100 stationary. In other embodiments, the user may alter the view taken by the operating microscope 100 while simultaneously altering the endoscopic view.

In one embodiment, the ocular viewing area displays both images in a picture-in-picture format, whereby one image is the primary image that takes up the entire ocular viewing area 110 (or external display) and the second image is the secondary images that is displayed overlapping in a smaller window in one corner of the ocular viewing area 110 (or external display). In such an embodiment, the user may toggle between the two images to change which image is the primary image. In an alternate embodiment, the ocular viewing area 110 (or external display) only displays one view to the user at a time (either the first view from the ocular lens 120, 122 of the operating microscope 100 or the second view from the endoscopic lens 210 of the endoscope 200), and the user may toggle back-and-forth between the two views. Further, in another embodiment, the two images may be displayed in equal sizes in a side by side manner, so that both images may be viewed equally at once. As discussed above, the switch between the images perceived by the microscope 100 and the endoscope 200 may be activated by an activation signal created by the processor/controller of the microscope 100 in response to a user input.

It should be noted that in the primary embodiment the image perceived by the ocular lens 120, 122 of the operating microscope 100 is an analog image and the image perceived by the endoscopic lens 210 of the endoscope 200 is a digital image. However, the invention is not so limited and in alternate embodiments either image may be an analog image and/or either image may be a digital image. Further, it is preferable that the image taken by the endoscope and/or the microscope (if digital), be of high definition resolution.

In one embodiment, the endoscope 200 may further comprise a light source. The light source may be configured at the end of the endoscope 200 comprising the lens 210. In one embodiment, the light source may be part of or within the lens 210 of the endoscope 200. The light source would enable the surgical area 400 to be illuminated and thereby enable the lens 210 to capture a clearer image of the surgical area 400. Further, the endoscope 200 would then bring a light closer to the target, thereby enhancing not only the view through the endoscopic display 112, but also the view captured by the lenses 220, 222 of the microscope 100.

As illustrated at least in FIGS. 1-4, the endoscope assembly 200 may be coupled to a surgical instrument 300 by means of at least one coupling mechanism 500. Although the use of two coupling mechanisms 500 is illustrated in FIG. 1, it should be noted that the invention is not so limited and in alternate embodiments more or less than two coupling mechanisms 500 may be used to couple the endoscope assembly 200 to a surgical instrument 300. For example, in the preferred embodiment, two coupling mechanisms 500 are used along the length of the instrument 300 to ensure that the lens 210 of the endoscope 200 sits behind the distal tip of the selected instrument 300. This helps to insure that the user may use the instrument 300 during operation without the endoscope 200 encumbering the user.

Figure 5:
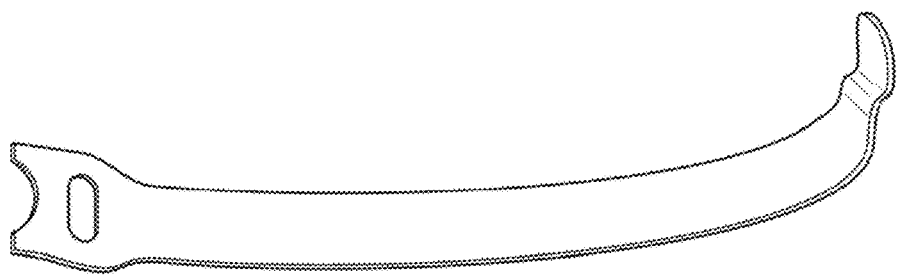
FIG. 5 is an inside view of a coupling mechanism according to one embodiment of the present invention.
Figure 6:
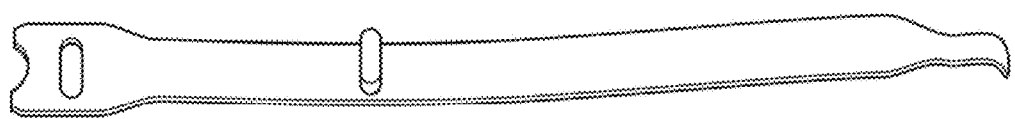
FIG. 6 is an outside view of a coupling mechanism according to one embodiment of the present invention.

Referring to FIGS. 5-6, an embodiment of the coupling mechanism 500 is illustrated. The coupling mechanism 500 comprises and inner surface and outer surface. As illustrated at least in FIGS. 2-4, the coupling mechanism is configured to wrap around both the endoscope 200 and a surgical instrument 300 to securely attach them together. The coupling mechanism 500 is further configured to be removable from both the endoscope 200 and surgical instrument 300 to provide the user with the ability to attach the endoscope 200 to other surgical instruments 300.

In another embodiment, the coupling mechanism 500 is disposable and comprises sterile Velcro® pads that are used to couple the endoscope 200 to and from a surgical instrument 300. In such embodiments, one corresponding portion of the Velcro® pad is securely attached to the surface of the endoscope 200 and the other corresponding portion of the Velcro® pad is attached to the surface of the surgical instrument 300. Therefore, the endoscope 200 may be attached to and removed from the surgical instrument 300 using the Velcro® pads. If a plurality of surgical instruments 300 are preconfigured with Velcro® pads, then the endoscope 200 may be easily exchanged and attached to the surgical instruments 300 as they are required during the operation.

In one embodiment, the Velcro® pads are attached to the surfaces of the endoscope 200 and the surgical instrument(s) 300 at various different points on the respective surfaces so as to have multiple potential connection positions for the endoscope 200 on the surgical instrument 300. This enables the endoscope 200 to be positioned at different points of the surgical instrument 300 and allows for greater customization of the endoscope/surgical instrument.

It should be noted that in alternate embodiments the coupling mechanism 500 may be secured by any other coupling means, so long as the endoscope 200 may be coupled to and removed from the surgical instrument 300. One benefit residing in that the user may attach the endoscope 200 to one surgical instrument 300 using at least one coupling mechanism 500, and then later, during the same procedure, attach the endoscope 200 to another surgical instrument 300 using the same or different coupling mechanisms 500. Therefore, the user may to move the endoscope to and from a plurality of surgical instruments during a single operational procedure, and thus may complete as many stages of the operation as they desire using the endoscope/microscope combination taught herein.

In one embodiment of the present invention, the width of the coupling mechanism 500 may be between 3 mm and 20 mm, and more preferably between 7 mm and 10 mm. Further, the length of the coupling mechanism 500 may be between 3 cm to 30 cm. However, it should be noted that the invention is not so limited and in alternate embodiments the coupling mechanism 500 may be any length or width deemed necessary to securely attach the endoscope 200 to a surgical instrument 300.

In the preferred embodiment, the coupling mechanism(s) 500 used to secure the endoscope to the surgical instrument is disposable. Therefore, the coupling mechanism(s) 500 are preferably thrown away after each use. The invention, however, is not so limited and in alternate embodiments the coupling mechanism(s) 500 may be reused for attachment of the endoscope 200 to more than one surgical instrument 300 during one operational procedure.

As noted above, one embodiment of the present invention relies on the mounting, clipping, wrapping, and/or attaching of the endoscope 200 to a surgical instrument 300, and to the insertion of the endoscopic image (taken from the lens 210 of the endoscope 200) into the endoscopic display 112 in the ocular viewing area 110 (or external display) of the operating microscope 100. This embodiment makes more efficient use of the endoscope 200 by not crowding the surgical space with new tools but rather transforming each and every surgical instrument 300 used in the surgery into an endoscope carrier. Further, since the images taken by the endoscope 200 are provided in the endoscopic display 112 within the ocular viewing area 110 of the operating microscope 100, the user does not have to take their eyes away from the ocular viewing area and may simultaneously view the surgical site 400 from multiple perspectives.

The endoscope/instrument combination may be inserted into the surgical area 400 at any time as the operating surgeon feels it is necessary. It should be noted that the use of the endoscope/instrument combination is not limited to operations also involving the use of the operating microscope 100, and may be employed in any body compartment whenever an endoscope may be used. Some non-limiting examples of operations where the present invention may be useful for an operating surgeon include: during operations on aneurysms once the aneurysm is exposed the endoscope/instrument combination may be helpful to look at the aneurysm back wall to clarify the vascular relationships;

during microvascular decompression operations the endoscope/instrument combination may reveal absence of vascular compression in areas not yet dissected, avoiding unnecessary dissections; during operation on tumor the endoscope/instrument combination may demonstrate residual tumor in areas not visible by the microscope alone; during spinal operation the endoscope/instrument combination may demonstrate nerve roots compression in areas not yet addressed surgically. It should be noted that the above are non-limiting examples of surgical situations where a surgeon may have use for the endoscope/instrument combination in conjunction with the operating microscope 100 described herein.

According to one embodiment of the present invention, the surgeon may ask an assistant to load the endoscope 200 on the preferred surgical instrument 300 (such as suction cannula, bipolar forceps, dissecting forceps, etc.) by applying at least one coupling mechanism 500 by at multiple points along the length of the endoscope 200 and surgical instrument 300 making sure that the tip of the endoscope 200 sits behind the tip of the selected instrument 300. For example, in one embodiment it may be preferable to have the endoscope 200 sit at least 5 mm behind the tip of the selected instrument. It should be noted that the invention is not so limited and in alternate embodiments the endoscope 200 may be positioned at or ahead of the tip of the selected instrument 300 so long as the endoscope 200 does not interfere with the user's use of the instrument 300 during the surgical proceeding.

Further, it should be noted that in alternated embodiments, the endoscope assembly 200 may be integrated with and be one in the same with the surgical instrument 300. Integrating the endoscope 200 with the surgical instrument 300 may be more costly, but may also provide for smaller and more exact instrument/endoscope tools.

In alternate embodiments of the present invention, the endoscope 200 may be used without being attached to a surgical instrument 300. This may be beneficial when the user just wants to look at a particular section of a surgical site 400 using both the operating microscope 100 and endoscope 200 without being encumbered by a surgical instrument 300.

In an alternate embodiment, the endoscope 200 may be disposable after each operation. If the endoscope 200 is not disposable, the endoscope 200 should be sterilizable.

It should be noted that the invention is not limited to the use of just one endoscope 200, and the in other alternate embodiments, more than one endoscope 200 may be used. In such embodiments, the ocular viewing area 110 may be configured to display more than two images at one time. For example, the ocular viewing area 110 may be configured to display images from the ocular lens 120, 122 of the operating microscope 100, along with a plurality of images from the plurality of endoscopes 200 or other data sets. For further example, in situations where the operating microscope 100 is not used in conjunction with the endoscope assemblies 200, the ocular viewing area 100 may be configured to display only images from a plurality of endoscopes 200.

Finally, it should be noted the an endoscope/operating microscope assembly system 1000 may be used during any type of surgery, such as but not limited to, intracranial surgery and spinal surgery.

Figure 7:
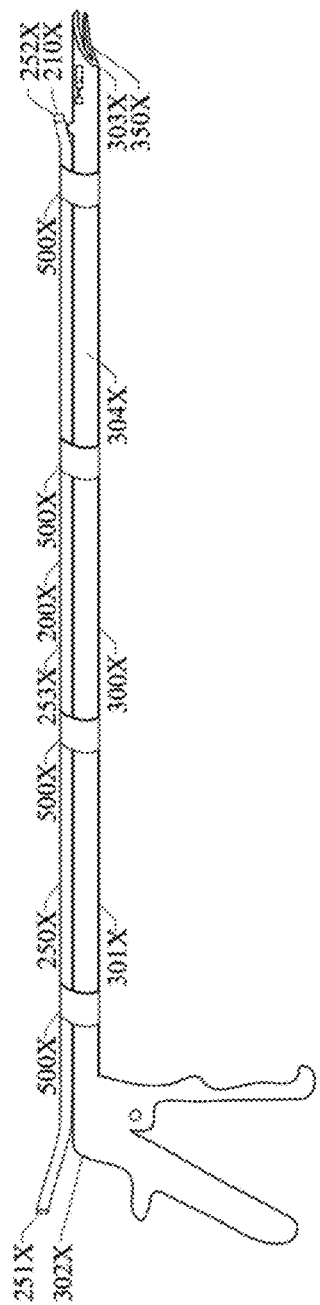
FIG. 7 is a schematic view of an endoscope mounted to a surgical instrument according to one embodiment of the present invention.

Referring to FIG. 7, an endoscope 200X mounted to a surgical instrument 300X according to one embodiment of the present invention is illustrated. The surgical instrument 300X and endoscope 200X of FIG. 7 are similar to the surgical instrument 300 and endoscope 200 discussed above with reference to FIGS. 1-4, therefore, like reference numbers are used to describe like components with the exception that the suffix "X" has been added. For purposes of simplicity, only the differences between the embodiments will be discussed below.

As exemplified, the endoscope 200X comprises a tubular body 250X and an endoscopic lens 210X. The tubular body 250X comprises a proximal end 251X, a distal end 252X, a tubular sleeve 253X, and an image fiber (shown in FIG. 19). As discussed in more detail below, the tubular sleeve 253X is the outer most layer of the tubular body 250 and comprises the image fiber within. The endoscopic lens 210X is coupled to the distal end 252X of the tubular body 250X and operably coupled to the image fiber. Although exemplified as a tubular body 250X, it should be noted that the invention is not so limited, and in alternate embodiments of the present invention, the tubular body 250X may take on any other shape.

The surgical instrument 300X comprises an elongated shaft 301X extending along a longitudinal axis A-A (shown in FIG. 8) from a proximal end 302X to a distal end 303X. The elongated shaft 301X comprises an outer longitudinal surface 304X that runs the entire length of the elongated shaft 301X. According to one embodiment of the present invention, the elongated shaft 301X is substantially rigid. However, the invention is not so limited, and in alternate embodiments, the elongated shaft 301X may be partially or completely flexible.

A working element 350X is coupled to the distal end 303X of the elongated shaft 301X. The working element 350X is a tool portion of the surgical instrument that engages, cuts, dissects, or otherwise manipulates tissue during surgical procedures. Examples of surgical instruments 300X include, but are not limited, to, suctions, dissectors, forceps, clamps, scissors, needle holders, bipolar coagulators, etc. Further, according to one embodiment of the present invention, the surgical instrument 300X is a micro-surgical instrument.

Figure 8:
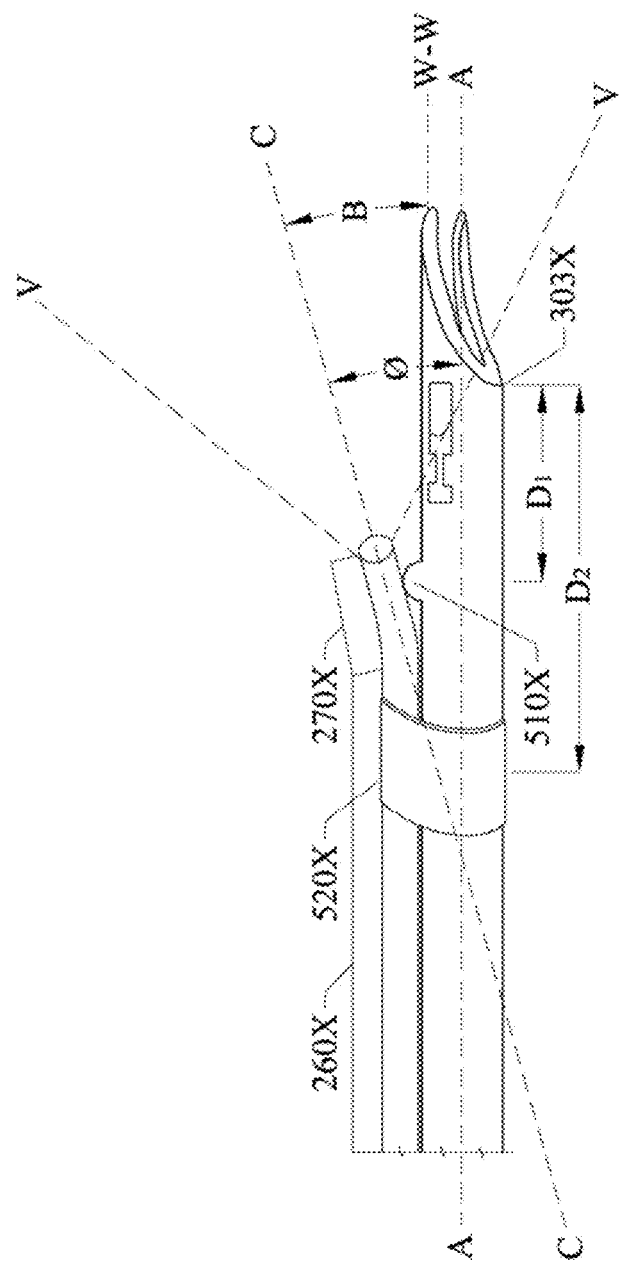
FIG. 8 is an enlarged view of the attached endoscope and surgical instrument of FIG. 7.

FIG. 8 illustrates an enlarged view of the attached endoscope 200X/surgical instrument 300X of FIG. 7. Referring to FIGS. 7 and 8 concurrently, the endoscope 200X is mounted to the outer longitudinal surface 304X of the elongate shaft 301X of the surgical instrument 300X so that the endoscopic lens 210X of the endoscope 200X protrudes (or diverges) from the outer longitudinal surface 304X of the elongated shaft 301X. As discussed in more detail below, the protrusion or divergence of the endoscopic lens 210X relative to the outer longitudinal surface 304X of the elongated shaft 301X ensures that the working element 350X only obstructs a portion, and not a majority, of the viewing field of the endoscopic lens. Therefore, when the user is performing surgery using the attached endoscope 200X/surgical instrument 300X, the images perceived by the endoscope provide a view of working element 350X, while remaining substantially unobstructed by the working element 350X. Thus, the user is provided with an enlarged perspective of the surgical site via the endoscopic lens 210X.

As shown, the tubular body 250X of the endoscope 200X comprises a base portion 260X and a protruding portion 270X. The base portion 260X is substantially orthogonal with and extends parallel to the longitudinal axis A-A of the elongated shaft 301X, while the protruding portion 270X is oblique to the longitudinal axis A-A of the elongated shaft 301X. Further, the protruding portion 270X comprises the distal end 252X of the tubular body 250X. The protruding portion 270X is oblique to the base portion 260X, which enables the endoscopic lens 210X to protrude or diverge from the outer longitudinal surface 304X of the elongated shaft 301X.

The endoscopic lens 210X of the endoscope 200X defines a viewing field V-V about a central axis C-C. In the exemplified embodiment of the present invention, the viewing field V-V is substantially conical in shape. However, the invention is not so limited, and in alternate embodiments of the present invention the viewing field V-V may take on other shapes.

Due, to the protruding portion 270X being oblique to the longitudinal axis A-A of the elongated shaft 301X, the central axis C-C of the viewing field V-V of the endoscopic lens 210X is also oblique to the longitudinal axis A-A of the elongated shaft 301X. Therefore, the central axis C-C of the viewing field V-V is oriented at an oblique angle θ to the longitudinal axis A-A of the elongated shaft 301X. Preferably, the oblique angle θ is between 3° to 75°. More preferably, the oblique angle θ is between 5° to 45°. Most preferably, the oblique angle θ is between 15° to 30°. Nonetheless, it should be noted that the invention is not limited to the central axis C-C being positioned at any specific oblique angle θ in all embodiments.

Also due to the protruding portion 270X being oblique to the longitudinal axis A-A of the elongated shaft 301X, the central axis C-C of the viewing field V-V of the endoscopic lens 210X is also oblique to the working axis W-W of the working element 350X. Therefore, the central axis C-C of the viewing field V-V is oriented at an oblique angle β to the working axis W-W of the working element 350X. Preferably, the oblique angle β is between 2° to 65°. More preferably, the oblique angle β is between 5° to 40°. Most preferably, the oblique angle β is between 13° to 25°. Nonetheless, it should be noted that the invention is not limited to the central axis C-C being positioned at any specific oblique angle β in all embodiments.

The central axis C-C of the viewing field V-V also intersects the outer longitudinal surface 304X of the elongated shaft 301X. Further, since the central axis C-C intersects the outer longitudinal surface 304X of the elongated shaft 301X, the central axis C-C of the viewing field V-V is substantially coplanar with the longitudinal axis A-A of the elongated shaft 301X. Finally, since the central axis C-C of the viewing field V-V of the endoscopic lens 210X is also oblique to the longitudinal axis A-A of the elongated shaft 301X, the working element 350X of the surgical instrument 300X is located within the viewing field V-V of the endoscopic lens 210X but separated from the central axis C-C of the endoscopic lens 210X by a distance $D_3$ (shown in FIG. 9).

As noted above and discussed in more detail below, the coupling mechanism 500X of the exemplified embodiment secures the endoscope 200X to the elongated shaft 301X so that the endoscopic lens 210X is substantially stationary relative to the elongated shaft 301X. In the exemplified embodiment, the coupling mechanism 500X comprises a protuberance 510X and a retaining member 520X. As discussed in more detail below, the combination of the protuberance 510X and the retaining member 520X is one way to create the oblique angle θ between the central axis C-C of the viewing field V-V and the longitudinal axis A-A of the elongated shaft 301X.

The protuberance 510X is located at a first longitudinal distance $D_1$ from the distal end 303X of the elongated shaft 300X. Further, the protuberance 510X extends from the outer longitudinal surface 304X of the elongated shaft 301X in a first transverse direction. In the exemplified embodiment, the first transverse direction is radially upward from the outer longitudinal surface 304X. However, the invention is not so limited and in other embodiments, the first transverse direction may be any direction that is radially outward from the outer longitudinal surface 304X.

The retaining member 520X secures the endoscope 200X to the elongated shaft 301X. In one embodiment of the present invention, the retaining member 520X may be similar to the coupling mechanism 500 as discussed above with reference to FIGS. 5 and 6. The retaining member 520X is located at a second longitudinal distance $D_2$ from the distal end 303X of the elongated shaft 301X. As shown in FIG. 8 and discussed in more detail below with reference to FIG. 10, the second longitudinal distance $D_2$ is greater than the first longitudinal distance $D_1$. Preferably, the retaining member 520X is made of a medical grade resilient material so as to create a compression fit around the tubular body 250X and the elongated shaft 301. However, the invention is not so limited, and in an alternate embodiment of the present invention, the retaining member 520X is made of a rigid medical grade plastic or metal.

Figure 9:
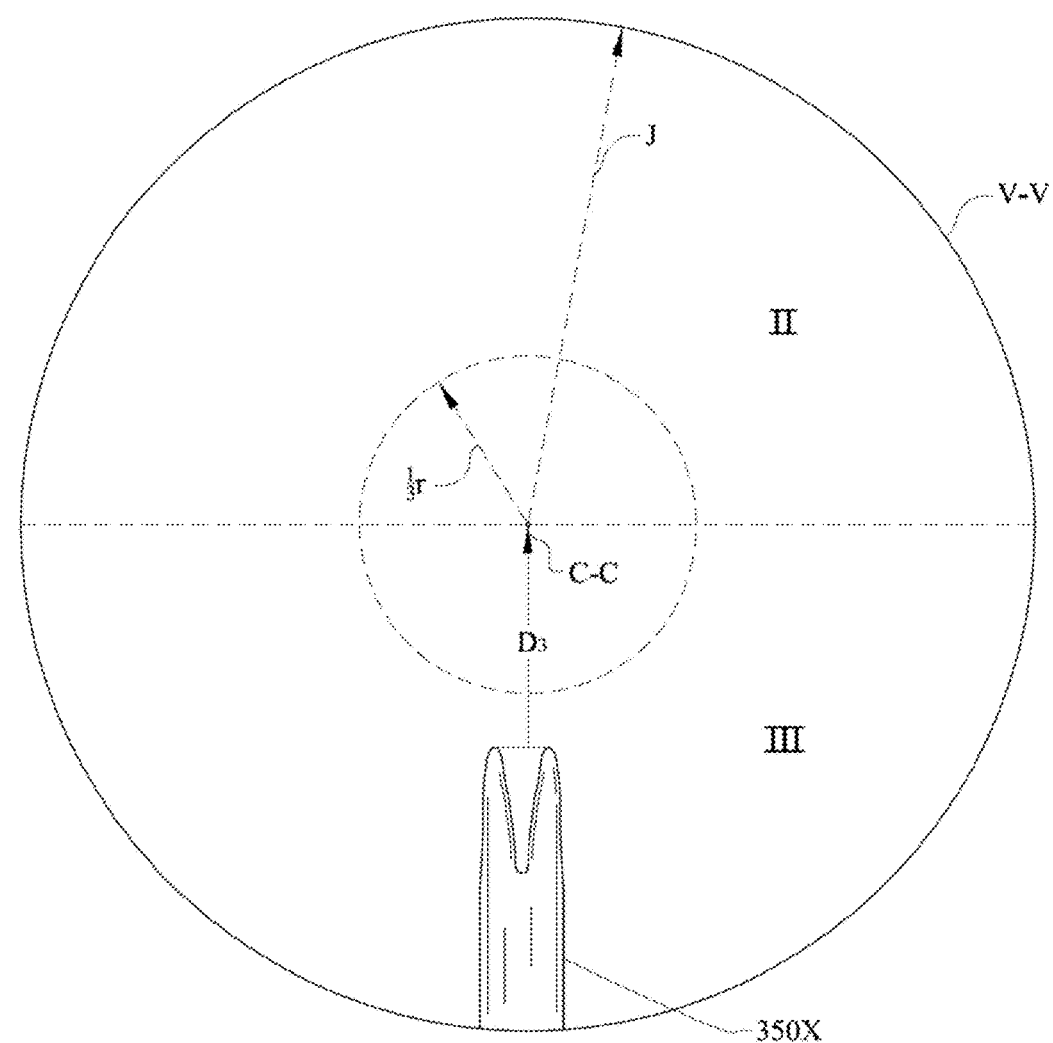
FIG. 9 is a view of the viewing field V-V from the perspective of the endoscopic lens.

Referring to FIG. 9, a view of the viewing field V-V from the perspective of the endoscopic lens 210X is illustrated. Since the viewing field V-V of the exemplified embodiment is substantially conical in shape, the view of FIG. 9 is circular in shape. However, as discussed above, the invention is not so limited and in alternate embodiments the viewing field V-V is not conical in shape, and therefore the view may not be circular in shape.

In the exemplified embodiment, the viewing field V-V comprises a central axis C-C, a radius r, an upper hemisphere II, and a lower hemisphere III. The angles θ, β are selected such that the working element 350X of the surgical tool 300X is positioned in the lower hemisphere III of the viewing field V-V. Further, it should be noted that the working element 350X obstructs only a minority of the lower hemisphere III. In the exemplified embodiment, the upper hemisphere II is the portion of the viewing field V-V that is above the central axis C-C and the lower hemisphere III is the portion of the viewing field V-V that is below the central axis C-C.

Since the central axis C-C of the viewing field V-V of the endoscopic lens 210X diverges from the working element 350X (and the longitudinal axis A-A), the working element 350X is at a distance $D_3$ from the central axis C-C. Further, the distance $D_3$ is preferably at least ⅓ r. Therefore, the inner one third (⅓) of the radius r of the viewing field V-V is free of the working element 350X, providing an unobstructed view of the surgical site for the user. However, in alternate embodiments of the present invention, the working element 350X may be located in both hemispheres II, III, may be located within the inner one third (⅓) of the radius r, and/or may obstruct a majority of the lower hemisphere III.

Figure 10:
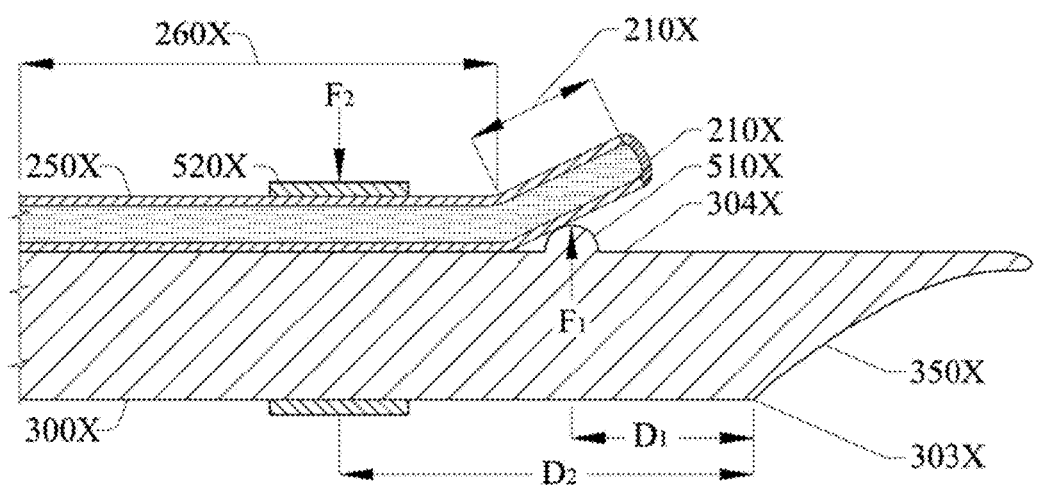
FIG. 10 is a schematic view of the endoscope mounted to the surgical instrument of FIGS. 7-9.

Referring to FIG. 10, a schematic of the endoscope 200X mounted to the surgical instrument 300X of FIGS. 7-9 is illustrated. As exemplified in FIG. 10, the coupling mechanism 500X comprises a protuberance 510X and a retaining member 520X. As discussed above with reference to FIG. 8, the protuberance 510X is located at a first longitudinal distance $D_1$ from the distal end 303X of the elongated shaft 301X, and extends from the outer longitudinal surface 304X of the elongated shaft 301X in a first transverse direction, the first transverse direction being radially upward from the outer longitudinal surface 304X. Further, the retaining member 520X secures the endoscope 200X to the elongated shaft 301X and is located at a second longitudinal distance $D_2$ from the distal end 303X of the elongated shaft 301X.

Finally, as noted above, the second longitudinal distance $D_2$ is greater than the first longitudinal distance $D_1$.

In the exemplified embodiment of FIG. 10, the endoscopic lens 210X (specifically, the central axis C-C of the viewing plan V-V of the endoscopic lens 210X) is diverged from the longitudinal axis A-A of the elongated shaft 301X and from the working element 350X through the use of a combination of the protuberance 510X and the retaining member 520X. Specifically, when a portion of the base portion 260X of the tubular body 250X resides on the outer longitudinal surface 304X of the elongated shaft 301X and under the retaining member 520X, and a portion of the tubular body 250X resides on the protuberance 510X, two substantially opposing forces are exerted on the tubular body 250X. The protuberance 510X exerts a first force $F_1$, while the retaining member 520X exerts a second force $F_2$, such that the first force $F_1$ and the second force $F_2$ are in substantially opposite directions. The exertion of the two forces $F_1$, $F_2$ results in the endoscopic lens 210X being diverged away from the longitudinal axis A-A of the elongated shaft 301X and from the working element 350. Stated another way, in such embodiments the protuberance 510X acts as a fulcrum on the tubular body 250X of the endoscope 200X that forces the protruding portion 270X (and endoscopic lens 210X) of the endoscope 200X to diverge from the outer longitudinal surface of the elongated shaft 301X.

Nonetheless, as discussed in more detail below, the divergence of the endoscopic lens 210X from the outer longitudinal surface of the elongated shaft 301X may be created using other embodiments of the coupling mechanism 500X.

Figure 11:
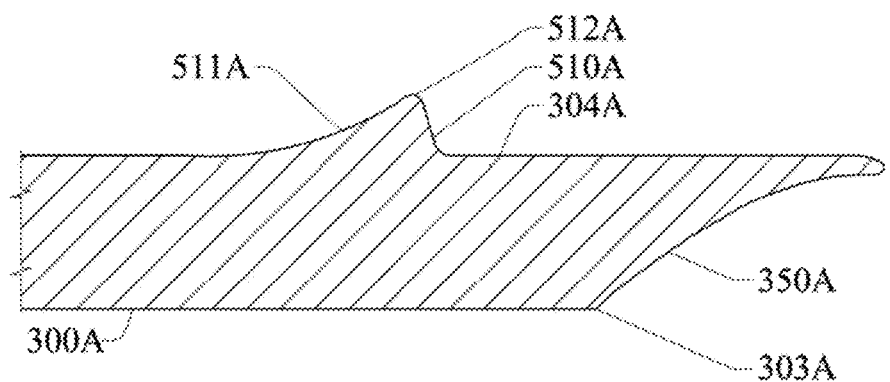
FIG. 11 is a schematic view of a protuberance according to an alternate embodiment of the present invention.
Figure 12:
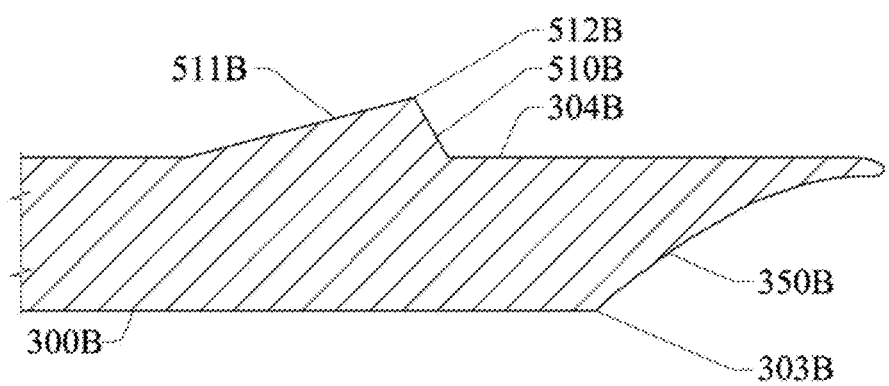
FIG. 12 is a schematic view of a protuberance according to an alternate embodiment of the present invention.

Referring to FIGS. 11-12, two examples of protuberances 510A, 510B according to two embodiments of the present invention are illustrated. The surgical instruments 300A. 300B of FIGS. 11-12 are similar to the surgical instrument 300X discussed above with reference to FIGS. 7-10, therefore, like reference numbers are used to describe like components with the exception that the suffix "A"/"B" has been used in place of the suffix "X." For purposes of simplicity, only the differences between the embodiments will be discussed below.

The protuberance 510A of FIG. 11 has a contoured surface 511A, so that the protuberance 510A may act as a ramp for the endoscope 200. As exemplified, the surface 511A is more specifically a concave surface. Further, in one embodiment, the protuberance 510A has a gradually increasing slope from the outer longitudinal surface 304A of the elongated shaft 301A to the peak 512A of the protuberance 510A. Although the peak 512A of the protuberance 510A is rounded, the invention is not so limited, and in other embodiments the peak 512A may be pointed.

The protuberance 510B of FIG. 12 has a linear surface 511B, so that the protuberance 510B may act as a ramp for the endoscope 200. As exemplified, the protuberance 510B has a constant slope from the outer longitudinal surface 304B of the elongated shaft 301B to the peak 512B of the protuberance 510. Although the peak 512B of the protuberance 510B is pointed, the invention is not so limited, and in other embodiments the peak 512B may be rounded.

Figure 13:
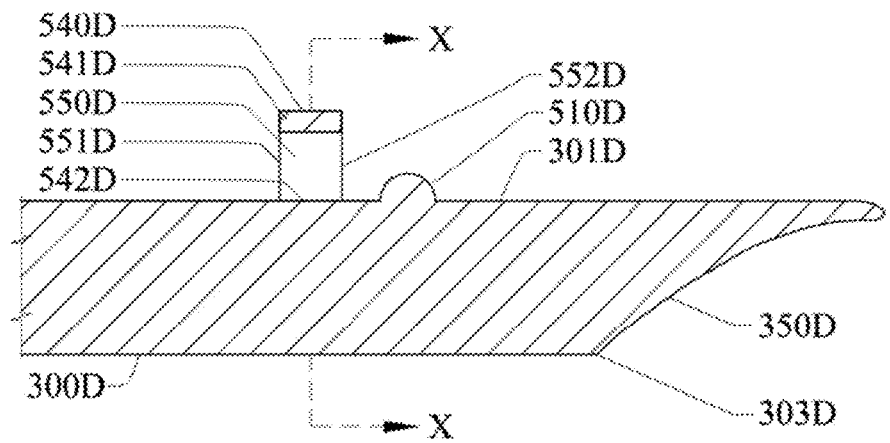
FIG. 13 is a cross-sectional schematic of a surgical instrument comprising an arch structure integrally formed therewith according to an alternate embodiment of the present invention.
Figure 14:
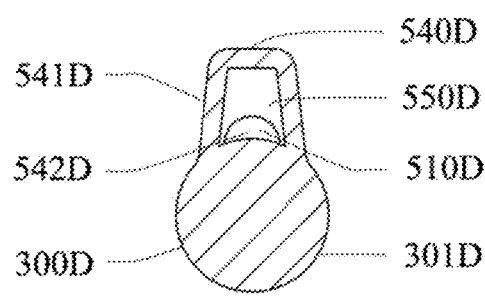
FIG. 14 is a cross-sectional view of the surgical instrument of FIG. 13 along the axis X-X.

Referring to FIGS. 13 and 14 concurrently, another alternative embodiment of the present invention will be discussed. Referring to FIG. 13, a cross-sectional schematic of a surgical instrument 300D comprising an arch structure 540D integrally formed therewith according to an embodiment of the present invention is illustrated. Referring to FIG. 14, a cross-sectional view of the surgical instrument 300D of FIG. 13 along the axis X-X is illustrated. The surgical instrument 300D of FIGS. 13-14 is similar to the surgical instrument 300X and endoscope 200X discussed above with reference to FIGS. 7-10, therefore, like reference numbers are used to describe like components with the exception that the suffix "D" has been added. For purposes of simplicity, only the differences between the embodiments will be discussed below.

The arch structure 540D is an open-ended arch structure that protrudes from and is integrally formed with the outer longitudinal surface 304D of the elongated shaft 301D of the surgical instrument 300D. The arch structure 540D defines a passageway 550D for retaining a portion of the endoscope 2000, and comprises a side wall 541D and a floor 542D. Further, the passageway 550D formed by the arch structure 540D comprises an entrance 551D and an exit 552D, both configured to receive the tubular body 250D of the endoscope 200D.

As discussed in more detail below, the transverse cross-section of the arch structure 540D is shaped and sized to accommodate the tubular body 250D of the endoscope 200D within the passageway 5500. According to one embodiment, the transverse cross-section is shaped and sized to create a tight fit between the inner surface of the side wall 541D and the tubular body 250D. However, the invention is not so limited, and in alternate embodiments of the present invention, the transverse cross section is sized and shaped to create a loose fit or a gap between the inner surface of the side wall 541D and the tubular body 250D.

Although not exemplified in FIGS. 13 and 14, the tubular body 250D of the endoscope 2000 may be inserted into the arch structure 540D via the entrance 551D of the passageway 550D. Upon insertion, the tubular body 250D will rest on the floor 542D of the arch structure 540D and within the passageway 550D. As discussed above, depending on the particular embodiment of the arch structure 540D, the tubular body 250D may, but does not necessarily, engage the inner surface of the side wall 541D. After the tubular body 250D is within the passageway 550D, the tubular body 250D may extend along the elongated shaft 301D until it is engages the protrusion 510D, which is located adjacent and just beyond the exit 552D of the passageway closest to the working element 350D. Once inside the passageway 550D, the side wall 541D of the arch structure 540D prevents relative rotational movement of the endoscope 200D around the surgical instrument 300D. More specifically, the side wall 541D prevents the endoscope 200D from becoming separated from the surgical instrument 300D. In this manner, the arch structure 540D acts as a retaining structure and retains the endoscope 200D on the surgical instrument 300D.

Upon engaging and extending over the protrusion 510D, the tubular body 250D of the endoscope 200D diverges away from the outer longitudinal surface 304D of the elongated shaft 301D. The arch structure 540D and protuberance 510D act in a manner similar to the retaining member 520X and protuberance 510X of FIG. 10. As such, the protuberance 510D exerts a first force $F_1$, while the arch structure 540D exerts a second force $F_2$, such that the first force $F_1$ and the second force $F_2$ are in substantially opposite directions. The exertion of the two forces $F_1$, $F_2$ results in the endoscopic lens 210D of the endoscope 200D being diverged away from the longitudinal axis A-A of the elongated shaft 301D and from the working element 350D. Therefore, the endoscope 200D may be positioned along the outer longitudinal surface 304D of the elongated shaft 301D in a position similar to that shown in FIGS. 7 and 8, whereby the central axis C-C of the viewing field V-V of the endoscope 200D is oblique to the longitudinal axis A-A of the elongated shaft 301D, and the working element 350D is located with the viewing field.

However, the invention is not so limited, and in an alternate embodiment of the present invention, the arch structure 540D does not exert a second force $F_2$ on the tubular body 250D of the endoscope 200D. In such embodiments, the tubular body 250D is still diverged away from the outer longitudinal surface 304D of the elongated shaft 301D, but the tubular body 250D does not come into contact with the inner surface of the side wall 541D.

In one embodiment of the present invention, the arch structure 540D is comprised of the same material as that of the elongated shaft 301D of the surgical instrument 300D. However, the invention is not so limited, and in alternate embodiments the arch structure 540D may be comprised of any suitable medical grade material, such as, but not limited to medical grade plastics and medical grade metals.

Figure 15:
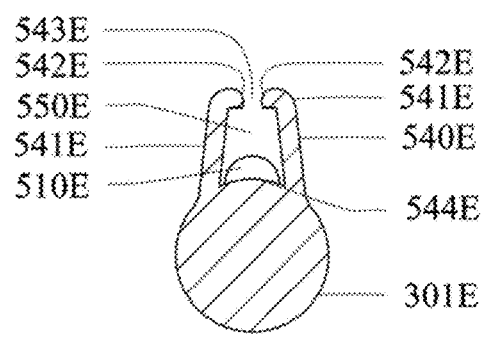
FIG. 15 is a cross-sectional view of an arch structure according to an alternate embodiment of the present invention.
Figure 16:
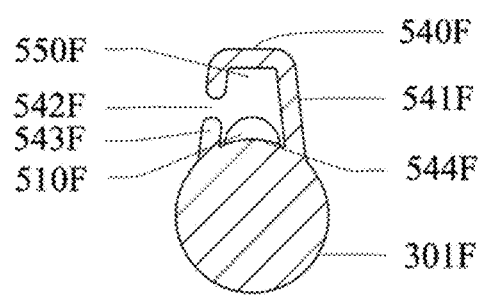
FIG. 16 is a cross-sectional view of an arch structure according to an alternate embodiment of the present invention.

Referring to FIGS. 15 and 16, cross-sectional views of arch structures 540E according to two alternate embodiments of the present invention are illustrated. The surgical instrument 300E of FIGS. 15 and 16 are similar to the surgical instrument 300D discussed above with reference to FIGS. 13-14, therefore, like reference numbers are used to describe like components with the exception that the suffix "E" has been added. For purposes of simplicity, only the differences between the embodiments will be discussed below.

The arch structure 540E of FIG. 15 is an open-ended arch structure that protrudes from and is integrally formed with the outer longitudinal surface 304E of the elongated shaft 301E of the surgical instrument 300E. The arch structure 540E defines a passageway 550E for retaining a portion of the endoscope 200E. The arch structure 540E comprises two side walls 541E, an open top end 543E, and a floor 544E. Further, each of the side walls 541E comprises a retaining nub 542E. Finally, similar to above and depending on the particular embodiment of the present invention, the transverse cross-section of the arch structure 540E may be such that a tight fit or a loose fit is created between the inner surface of the two side walls 541E and the tubular body 250E of an endoscope 200E.

The tubular body 250E of the endoscope 200E may be inserted into the arch structure 540E via the open top end 543E. Upon insertion, the tubular body 250E will rest on the floor 544E of the arch structure 540E and within the passageway 550E. As discussed above, depending on the particular embodiment of the arch structure 540E, the tubular body 250E may, but does not necessarily, engage the inner surface of the two side walls 541E. After the tubular body 250E is within the passageway 550E, the tubular body 250 may extend along the elongated shaft 301E until it engages the protrusion 510E, which is located adjacent to and just beyond an exit of the passageway 550E closest to the working element 350E. Upon engaging and extending over the protrusion 510E, the tubular body 250E of the endoscope 200E diverges away from the outer longitudinal surface 304E of the elongated shaft 301E.

Further, it should be noted that when the endoscope 200E is positioned within the passageway 550E, the side walls 541E of the arch structure 540E prevent relative rotational movement of the endoscope 200E around the surgical instrument 300E. Similarly, the retaining nubs 542E prevent the endoscope 200E from unintentionally exiting the arch structure 540E via the open top end 543E.

The arch structure 540F of FIG. 16 is a c-clamp arch structure 540F that protrudes from and is integrally formed with the outer longitudinal surface 304F of the elongated shaft 301F of the surgical instrument 300F. Similarly, the arch structure 540F defines a passageway 550F for retaining a portion of the endoscope 200F. The arch structure 540F comprises a hook-shaped wall 541F, an opening 542F, a retaining nub 543F, and a floor 544F. Finally, similar to above and depending on the particular embodiment of the present invention, the transverse cross-section of the arch structure 540F may be such that a tight fit or a loose fit is created between the inner surface of the hook-shaped wall 541F and the tubular body 250F of an endoscope 200F.

The tubular body 250F of the endoscope 200F may be inserted into the arch structure 540F via the opening 542F. Upon insertion, the tubular body 250F will rest on the floor 544F of the arch structure 540F and within the passageway 550F. As discussed above, depending on the particular embodiment of the arch structure 540F, the tubular body 250F may, but does not necessarily, engage the inner surface of the hook-shaped wall 541F. After the tubular body 250F is within the passageway 550F, the tubular body 250F may extend along the elongated shaft 301F until it is engages the protrusion 510F, which is located adjacent an exit of the passageway closest to the working element 350F. Upon engaging and extending over the protrusion 510F, the tubular body 250F of the endoscope 200F diverges away from the outer longitudinal surface 304F of the elongated shaft 301F.

Further, it should be noted that when the endoscope 200F is within the passageway 550, the hook-shaped wall 541F of the arch structure 540F prevents relative vertical movement and relative rotational movement of the endoscope 200F in directions opposing the opening 542F. The retaining nub 543F of the arch structure 540F prevents the endoscope 200F from unintentionally exiting the passageway 550F via the opening 542F.

Figure 17:
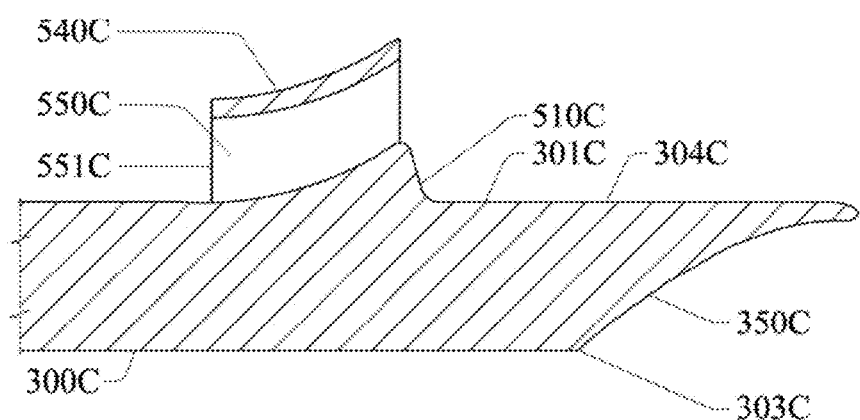
FIG. 17 is a cross-sectional schematic of a surgical instrument comprising an arch structure integrally formed therewith according to an alternate embodiment of the present invention.

Referring to FIG. 17, a cross-sectional schematic of a surgical instrument 300C comprising an arch structure 540C integrally formed therewith according to an alternate embodiment of the present invention is illustrated. The surgical instrument 300C of FIG. 17 is similar to the surgical instrument 300D and endoscope 200D discussed above with reference to FIGS. 13-14, therefore, like reference numbers are used to describe like components with the exception that the suffix "C" has been added. For purposes of simplicity, only the differences between the two embodiments will be discussed below.

Unlike the embodiment of FIGS. 13-14, the embodiment of FIG. 17 comprises a protuberance 510C that resides at least partially within the passageway 550C created by the arch structure 540C. Therefore, as opposed to the embodiment described above with reference to FIGS. 13-14, the protuberance 510C is not located adjacent an exit of the passageway 550C, but at least partially within the passageway 550C. It should be noted that in one embodiment of the present invention, the protuberance 510C resides entirely within the passageway 550C, while in another embodiment of the present invention, the protuberance 510C resides only partially within the passageway 550C.

As exemplified, the arch structure 540C is sloped in the longitudinal direction in a manner similar to that of the slope of the protuberance 510C. This allows for the tubular body 250C of the endoscope 200C to be inserted into the arch structure 540 via the entrance 551C of the passageway 550C, extend along the elongated shaft 301C until it is engages the protrusion 510C, and diverge away from the outer longitudinal surface 304C of the elongated shaft 301C. By sloping the arch structure 540C in a manner similar to the slope of the protuberance 510C, the inner surface of the arch structure 540C may form a tight fit around the tubular body 250C of the endoscope 200C to more securely hold the endoscope 200C in place. Nonetheless, it should be noted that the invention is not so limited, and in alternate embodiments of the present invention, the slope of the arch structure 540C may be omitted or may be greater or less than the slope of the protuberance 510C.

Figure 18:
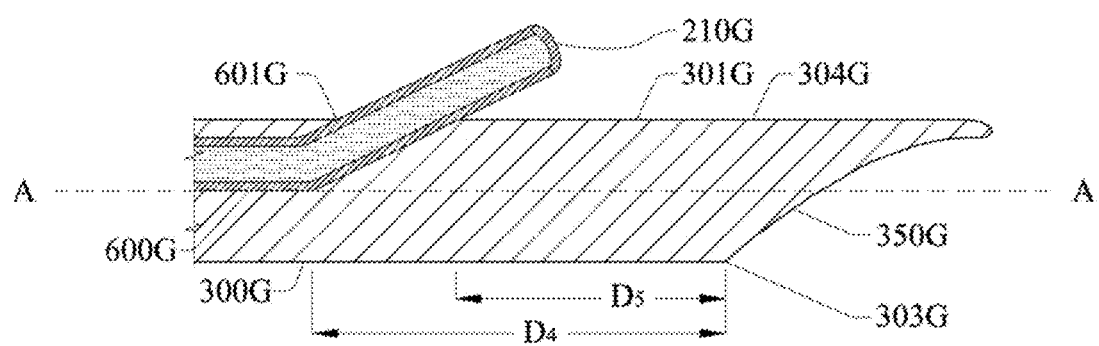
FIG. 18 is a cross-sectional schematic of a surgical instrument comprising a channel integrally formed therein according to an alternate embodiment of the present invention.

Referring to FIG. 18, a cross-sectional schematic of a surgical instrument 300G comprising a channel 600G integrally formed therein according to one embodiment of the present invention is illustrated. The surgical instrument 300G of FIG. 18 is similar to the surgical instrument 300X discussed above with reference to FIGS. 7-10, therefore, like reference numbers are used to describe like components with the exception that the suffix "G" has been added. For purposes of simplicity, only the differences between the embodiments will be discussed below.

As exemplified, the surgical instrument 300G comprises a channel 600G that defines a passageway for retaining a portion of the endoscope 200G. The channel 600G extends longitudinally along the axis A-A of the elongated shaft 301G prior to sloping obliquely to the axis A-A at a distance $D_4$ from the distal end 303G of the elongated shaft 301G. After the channel 600G slopes obliquely to the axis A-A, the channel 600G exits the outer longitudinal surface 304G at an exit point 601G, the exit point 601G being at a distance $D_5$ from the distal end 303G of the elongated shaft 3016. It should be noted that the present invention is not limited to any specific distance $D_4$, distance $D_5$, or slope of the channel 600G.

As exemplified, the passageway of the channel 600G is configured to retain the tubular body 250G of an endoscope 200G. The interior of the channel 600G prevents relative rotational movement and relative transverse movement of the tubular body 250G about the elongated shaft 301G. Preferably, the interior of the channel 600G forms a tight fit around the tubular body 250G. However, the invention is not so limited, and in alternate embodiments, the interior of the channel 600G may form a loose fit around the tubular body 250G.

Figure 19:
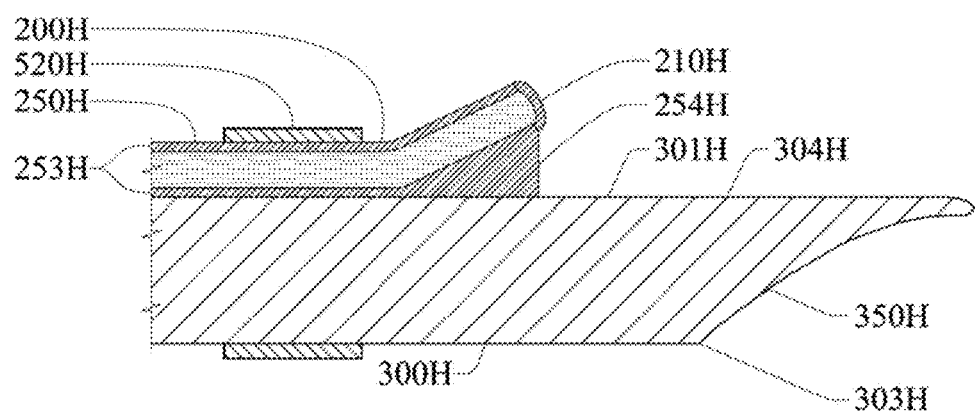
FIG. 19 is a cross-sectional schematic of a surgical instrument and an endoscope according to an alternate embodiment of the present invention.

Referring to FIG. 19, a cross-sectional schematic of a surgical instrument 300H and an endoscope 200I according to one embodiment of the present invention is illustrated. The surgical instrument 300H and endoscope 200H of FIG. 19 is similar to the surgical instrument 300X and endoscope 200X discussed above with reference to FIGS. 7-10, therefore, like reference numbers are used to describe like components with the exception that the suffix "H" has been added. For purposes of simplicity, only the differences between the embodiments will be discussed below.

As shown, the endoscope 200H of FIG. 19 comprises a tubular body 250H and an endoscopic lens 210H. The tubular body 250H comprises a tubular sleeve 253H and an image fiber 255H. Generally, the tubular sleeve 253H is a casing that encapsulates the image fiber 255H. Preferably, the tubular sleeve 253H is made of a flexible, medical grade, resilient material so to create a compression fit around the image fiber 255H of the endoscope 200H. However, the invention is not so limited, and in alternate embodiments of the present invention, the tubular sleeve 253H may be made of a rigid medical grade plastic or metal.

The tubular sleeve 253H of FIG. 19 comprises a block 254H. As described below, the block 254H may be conceptualized as a ramp or protuberance. Preferably, the block 254H is integrally formed with the tubular sleeve 253H. However, the invention is not so limited, and in alternate embodiments of the present invention the block 254H may be integrally formed with the outer longitudinal surface 304H of the elongated shaft 301H, or may be a separate component that may be secured to one or more of the tubular sleeve 253H and the outer longitudinal surface 304H of the elongated shaft 301H.

As exemplified, during operation a retaining member 520H secures the endoscope 200H to the elongated shaft 301H. In such instances, the block 254H is configured between the endoscopic lens 210H and the outer longitudinal surface 304H, so that the block 254H diverges the endoscopic lens 210H away from the outer longitudinal surface 304H of the elongated shaft 301H and from the working element 350H. As such, the central axis C-C of the viewing field V-V of the endoscope 200H is oblique to the longitudinal axis A-A of the elongated shaft 301H.

Although exemplified as part of the tubular sleeve 253H, in alternate embodiments of the present invention, the block 254H may be formed integrally with the elongated shaft 301H of the surgical tool 300H, or may be a separate component that is secured to one or more of the elongated shaft 301H and the tubular sleeve 253H.

Figure 20:
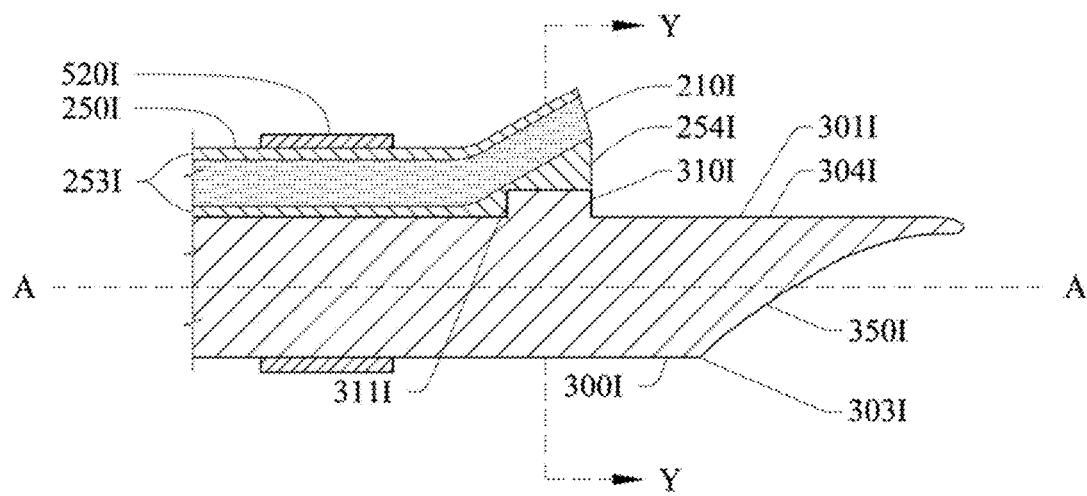
FIG. 20 is a cross-sectional schematic of a surgical instrument and an endoscope according to an alternate embodiment of the present invention.
Figure 21:
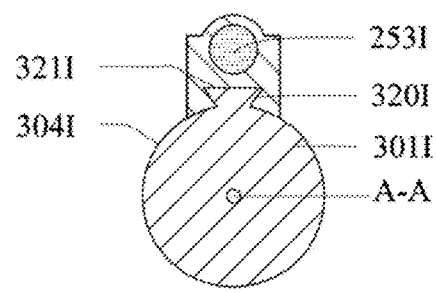
FIG. 21 is a cross-sectional view of the surgical instrument and endoscope of FIG. 20 along the axis Y-Y.

Referring to FIG. 20, a cross-sectional schematic of a surgical instrument 300I and an endoscope 200I according to an alternate embodiment of the present invention is illustrated. Referring to FIG. 21, a cross-section of the surgical instrument 300I and endoscope 200I of FIG. 20 along the axis V-V is illustrated. The surgical instrument 300I of FIG. 20 is similar to the surgical instrument 300X and endoscope 200X discussed above with reference to FIG. 19, therefore, like reference numbers are used to describe like components with the exception that the suffix "I" has been added. For purposes of simplicity, only the differences between the embodiments will be discussed below.

As shown in FIGS. 20-21, the surgical instrument 300I further comprises a blockade 310I and a first indexing feature 320I, while the endoscope 200I further comprises a second indexing feature 321I. The first indexing feature 320I extends longitudinally along the outer longitudinal surface 304I of the elongated rod 301I. Similarly, the second indexing feature 321I extends longitudinally along the tubular sleeve 353I of the endoscope 200I. In the exemplified embodiments, the first indexing feature 320I is made of the same material and integrally formed in the outer longitudinal surface 304 of the elongated rod 301. Similarly, the second indexing feature 321I is integrally formed in the tubular sleeve 353 of the endoscope 200. Finally, as discussed in more detail below, the blockade 310I comprises a transverse wall 311I.

In the exemplified embodiment, the first indexing feature 320I is a longitudinal rib and the second indexing feature 321I is a longitudinal groove. More specifically, the first indexing feature 320I is a dovetail shaped rib, while the second indexing feature 321I is a dovetail shaped groove. However, it should be noted that the invention is not so limited, and in alternate embodiments, the first and second indexing features 320I, 321I may be any shape, such as but not limited to, T-shaped, V-shaped, or L-shaped rib. Nonetheless, it should be noted that the first and second indexing features 320I, 321I should be corresponding shapes so that they may mate with one another. Further, in alternate embodiments of the present invention, the first indexing feature 320I may be a longitudinal groove, while the second indexing feature 321I is a longitudinal rib. Therefore, the invention is not limited to whether the first or second indexing features 320I, 321I are a longitudinal groove and longitudinal rib respectively.

As shown in FIG. 21, the first indexing feature 320I and the second indexing feature mate with one another so that the first indexing feature 320I may be inserted into and slid longitudinally along the second indexing feature 321I. Once the first indexing feature 320I is mated with the second indexing feature 321I, the endoscope 200I is mounted to the outer longitudinal surface 304I of the elongated shaft 301I. The second indexing feature 321I of the tubular body 250I (specifically, the tubular sleeve 253I) may then be slid along the first indexing feature 320I until the second indexing feature 321I contacts the transverse wall 311I of the blockade 310I. As such, the blockade 310I acts as a barrier to prevent additional longitudinal movement of the second indexing feature 321I along the outer longitudinal surface 304I of the elongated shaft 301I. When mated, the first and second indexing features 320I, 321I prevent rotation of the tubular body 250I relative to the elongated shaft 301I. Further, it should be noted that the working element 350I is located within the viewing field V-V of the endoscopic lens 210I when the first and second indexing features 320I, 321I are mated with one another and the second indexing feature 321I is in contact with the transverse wall 311I of the blockade 310I. Such a configuration provides the user with a more consistent and stable view of the working element 350I via the endoscopic lens 210I.

Finally, although a retaining member 520I is illustrated, the invention is not so limited, and in alternate embodiments the retaining member 520I may be omitted. Further, although the tubular sleeve 253I comprises block 254I, the invention is not so limited, and in alternate embodiments, the block 254I may be omitted. In such embodiments, the endoscopic lens 210I is not diverged away from the outer longitudinal surface 304 of the elongated shaft 301.

Figure 22:
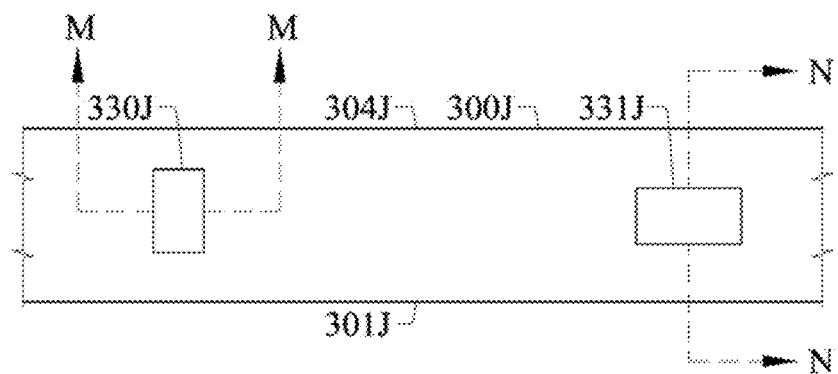
FIG. 22 is a cross-sectional schematic of a surgical tool according to an alternate embodiment of the present invention.
Figure 23:
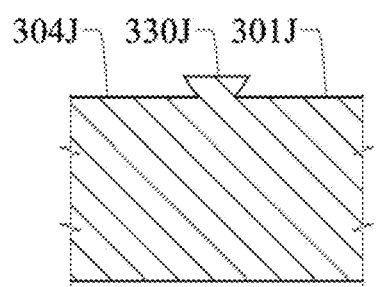
FIG. 23 is a cross-sectional view of the surgical instrument of FIG. 22 along the axis M-M.
Figure 24:
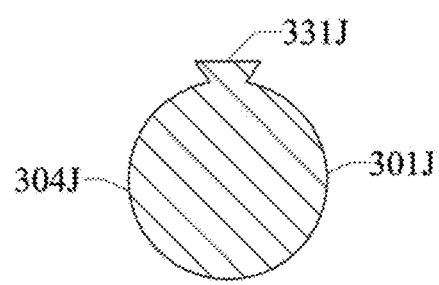
FIG. 24 is a cross-sectional view of the surgical instrument of FIG. 22 along the axis N-N.

FIGS. 22-29 will now be discussed concurrently. Referring to FIG. 22 a schematic of a surgical instrument 300J according to an alternate embodiment of the present invention is illustrated. Referring to FIG. 23, a cross-section of the surgical instrument 300J of FIG. 22 along the axis M-M is illustrated. Referring to FIG. 24, a cross-section of the surgical instrument 300J of FIG. 22 along the axis N-N is illustrated. The surgical instrument 300J of FIGS. 22-24 is similar to the surgical instrument 300X discussed above with reference to FIGS. 7-10, therefore, like reference numbers are used to describe like components with the exception that the suffix "J" has been added. For purposes of simplicity, only the differences between the embodiments will be discussed below.

The surgical instrument 300J comprises both a lateral indexing rib 330J and a longitudinal indexing rib 331J raised off and protruding from the outer longitudinal surface 304. As discussed in more detail below, the lateral and longitudinal indexing ribs 330J, 331J are configured to mate with corresponding slots 280J, 281J on the endoscope 200J, such that the transverse and longitudinal movement of the endoscope 200J with respect to the surgical instrument 300J is restricted.

As shown in FIG. 23, the lateral indexing rib 330J comprises an upper surface 334J and two flanges 332J. The upper surface 334J is substantially parallel with the outer longitudinal surface 304 of the elongated shaft 301, while the flanges 332J are oblique to both the upper surface 334J and the outer longitudinal surface 304. Further, as shown in FIG. 24, the longitudinal indexing rib 331J comprises an upper surface 335J and two flanges 333J. The upper surface 335J is substantially parallel with the outer longitudinal surface 304 of the elongated shaft 301, while the flanges 333J are oblique to both the upper surface 335J and the outer longitudinal surface 304. The longitudinal indexing rib 331J is substantially similar to the lateral indexing rib 330J, with the exception that the indexing ribs 330J, 331J are offset by 90° with respect to one another.

More specifically, in the exemplified embodiment the lateral indexing rib 330J and the longitudinal indexing rib 331J are dovetail shaped ribs. However, it should be noted that the invention is not so limited, and in alternate embodiments, the lateral indexing rib 330J and the longitudinal indexing rib 331J may be any shape, such as but not limited to, T-shaped, V-shaped, or L-shaped ribs.

Figure 25:
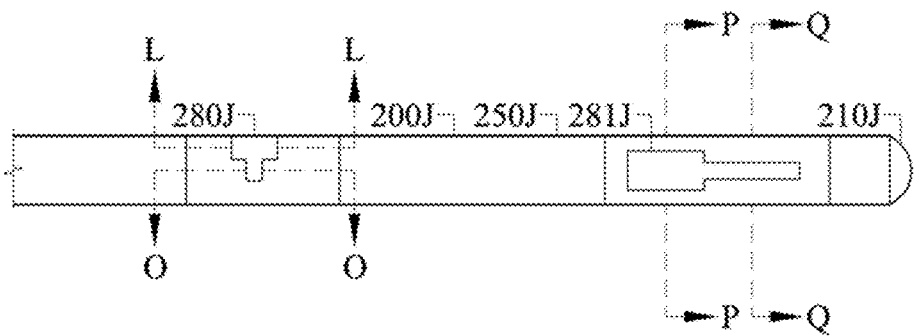
FIG. 25 is a cross-sectional schematic of an endoscope according to an alternate embodiment of the present invention.
Figure 26:
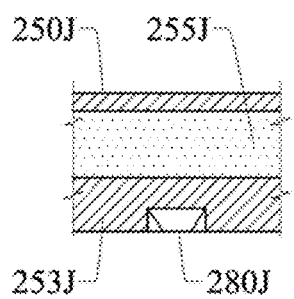
FIG. 26 is a cross-sectional view of the endoscope of FIG. 25 along the axis L-L.
Figure 27:
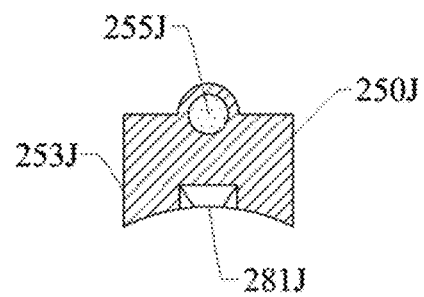
FIG. 27 is a cross-sectional view of the endoscope of FIG. 25 along the axis P-P.
Figure 28:
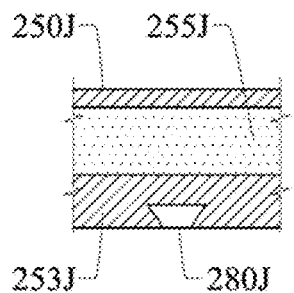
FIG. 28 is a cross-sectional view of the endoscope of FIG. 25 along the axis O-O.
Figure 29:
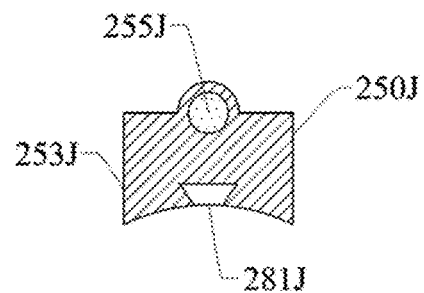
FIG. 29 is a cross-sectional view of the endoscope of FIG. 25 along the axis Q-Q.

Referring to FIG. 25 a schematic of an endoscope 200J according to an alternate embodiment of the present invention is illustrated. Referring to FIG. 26, a cross-section of the endoscope 200J of FIG. 25 along the axis L-L is illustrated. Referring to FIG. 27, a cross-section of the endoscope 200J of FIG. 25 along the axis P-P is illustrated. Referring to FIG. 28, a cross-section of the endoscope 200J of FIG. 25 along the axis O-O is illustrated. Referring to FIG. 29, a cross-section of the endoscope 200J of FIG. 25 along the axis Q-Q is illustrated. The endoscope 300J of FIGS. 25-29 is similar to the endoscope 200X discussed above with reference to FIGS. 7-10, therefore, like reference numbers are used to describe like components with the exception that the suffix "J" has been added. For purposes of simplicity, only the differences between the embodiments will be discussed below.

The endoscope 200J comprises a lateral slot 280J and a longitudinal slot 281J. The lateral slot 280J comprises an entry section 282J and a retaining section 283J. Similarly, the longitudinal slot 281J comprises an entry section 284J and a retaining section 285J. As discussed in more detail below, the entry sections 282J, 284J are configured to allow for the insertion of the indexing ribs 330J, 331J into the lateral and longitudinal slots 280J, 281J respectively, while the retaining sections 283J, 285J are configured for the locking and restricting of the lateral and longitudinal slots 280J, 281J in place. The lateral slot 280J is substantially similar to the longitudinal slot 281J, with the exception that the slots 280J, 281J are offset by 90° with respect to one another.

As shown in FIGS. 26 and 28, the entry section 282J has a cross-sectional shape of a rectangle, while the retaining section 283J has a cross-sectional shape of a dovetail. As discussed in more detail below, the retaining section 283J comprises shoulders 286J that coincide with the flanges 332J of the lateral indexing rib 330J. Similarly, and as shown in FIGS. 27 and 29, the entry section 284J has a cross-sectional shape of a rectangle, while the retaining section 285J has a cross-sectional shape of a dovetail. As also discussed in more detail below, the retaining section 285J comprises shoulders 287J that coincide with the flanges 333J of the lateral indexing rib 331J.

However, it should be noted that the invention is not so limited, and in alternate embodiments, the entry sections 282J, 284J may be any shape, so long as the entry sections 282J, 284J are equal to or larger than the indexing ribs 330J, 331J, and therefore allows for the insertion of the indexing ribs 330J, 331J into the lateral and longitudinal slots 280J, 281J. Further, in alternate embodiments, the retaining sections 283J, 285J may be any shape, such as but not limited to, T-shaped, V-shaped, or L-shaped. However, the retaining sections 283J, 285J should be sized and shaped similar to the indexing ribs 330J, 331J, so that the indexing ribs 330J, 331J and the retaining sections 283J, 285J may form a tight fit assembly.

Although not exemplified, the invention of FIGS. 22-29 is configured such that in order to mate the surgical tool 300J with the endoscope 200J, the longitudinal indexing rib 331J is first inserted into the entry section 284J of the longitudinal slot 281J. Next, the longitudinal indexing rib 331J is slid in the longitudinal direction from the entry section 284J and into the retaining section 285J of the longitudinal slot 281J. Thereafter, the lateral indexing rib 330J is then inserted into the entry section 282J of the lateral slot 280J. Once the lateral indexing rib 330J is inserted into the entry section 282J of the lateral slot 280J, the lateral indexing rib 330J is slid transversely into the retaining section 283J of the lateral slot 280J. Thus, due to the configurations of the longitudinal and lateral slots 280J, 281J, the longitudinal indexing rib 331J is first mated with the longitudinal slot 281J prior to the lateral indexing rib 330J being mated with the lateral slot 280J.

Since the cross-sectional shapes of the indexing ribs 330J, 331J are substantially the same shape and size as the retaining sections 283J, 285J (as can be seen in FIGS. 23, 24, 28, and 29), the flanges 332J, 333J of the indexing ribs 330J, 331J engage the shoulders 286J, 287J of the retaining sections 283J, 285J respectively. Specifically, the flange 332J of the lateral indexing rib 330J engages the shoulder 286J of the retaining section 283J of the lateral slot 280J, while the flange 333J of the longitudinal indexing rib 331J engages the shoulder 287J of the retaining section 285J of the longitudinal slot 281J. This creates a tight fit assembly between the indexing ribs 330J, 331J and the slots 280J, 281J respectively. Further, once the indexing ribs 330J, 331J are mated with the slots 280J, 281J, the endoscope 200J is mounted to the outer longitudinal surface 304J of the elongated shaft 301J.

When mated, the indexing ribs 330J, 331J and slots 280J, 281J prevent relative rotational movement and relative transverse movement of the tubular body 250J relative to the elongated shaft 301J. Further, it should be noted that the working element (not shown) is located within the viewing field V-V of the endoscopic lens 210J. Such a configuration provides the user with a more consistent and stable view of the working element via the endoscopic lens 210J.

In the preferred embodiment, the indexing ribs 330J, 331J are constructed from the same material as the surgical instrument 300J and the slots 280J, 281J are constructed from the same material as the endoscope 200J. However, the invention is not so limited, and in alternate embodiments, the indexing ribs 330J, 331J and/or the slots 280J, 281J may be constructed from any medical grade material. For instance, in one embodiment, the indexing ribs 330J, 331J and/or the slots 280J, 281J are constructed from a resilient material for a compression fit.

In an alternate embodiment of the present invention, the lateral and longitudinal slots 280J, 281J further comprise dimples. The dimples would be configured within the retaining portions 283J, 285J of the slots 280J, 281J and would prevent unintentional removal of the indexing ribs 330J, 331J from the slots 280J, 281J. Specifically, the dimples would create a tighter fit mating between the indexing ribs 330J, 331J and the slots 280J, 281J so that the indexing ribs 330J, 331J are not unintentionally slid from the retaining portions 283J, 285J to the entry sections 282J, 284J.

Generally, the indexing ribs 330J, 331J may be conceptualized as a first indexing feature, while the slots 280J, 281J may be conceptualized as a second indexing feature. Similar to that which has been discussed above, it should be noted that the first and second indexing features should be corresponding shapes so that they may mate with one another.

Further, in alternate embodiments of the present invention, the first indexing feature may be slots, while the second indexing feature is indexing ribs. Therefore, the invention is not limited to whether the first or second indexing features are ribs and slots respectively.

Further, although the tubular body 250J of the endoscope 200J does not comprise a block (as shown above with reference to FIGS. 19-21), the invention is not so limited, and in alternate embodiments, the block may be included in the tubular body 250J of endoscope 200J. In such embodiments, the endoscopic lens 210J is will be diverged away from the outer longitudinal surface 304J of the elongated shaft 301J of the surgical tool 300J. Moreover, although the outer longitudinal surface 304J of the elongated shaft 301J of the surgical tool 300J does not comprise a protuberance (as shown above with reference to FIGS. 7-8 and 10-12), the invention is not so limited, and in alternate embodiments, the protuberance may be included in the outer longitudinal surface 304J of the elongated shaft 301J. In such embodiments, the endoscopic lens 210J will be diverged away from the outer longitudinal surface 304J of the elongated shall 301J of the surgical tool 300J.

Finally, it should be noted that any of the embodiments of surgical tools and endoscopes discussed above may be used as a surgical apparatus in a surgical system in conjunction with a microscope and a display, similar to that discussed above with reference to FIG. 1. Therefore, the surgical instrument 300 and the endoscope 200 of the endoscope/operating microscope assembly system (or surgical system) 1000 of FIG. 1 may be substituted out with any of the alternate surgical instruments 300X, A-J and endoscopes 200X, A-J discussed above with reference to FIGS. 7-29.

While the embodiment of the present invention has been described with reference to the accompanying drawings, it can be understood by those skilled in the art that the present invention can be embodied in other specific forms without departing from its spirit or essential characteristics. Therefore, the foregoing embodiments and advantages are merely exemplary and are not to be construed as limiting the present invention. The present teaching can be readily applied to other types of apparatuses. The description of the foregoing embodiments is intended to be illustrative, and not to limit the scope of the claims. Many alternatives, modifications, and variations will be apparent to those skilled in the art. In the claims, means-plus-function clauses are intended to cover the structures described herein as performing the recited function and not only structural equivalents but also equivalent structures.

What is claimed is:

1. A surgical apparatus comprising:
   a surgical instrument comprising an elongated shaft extending along a longitudinal axis from a proximal end to a distal end, a working element coupled to the distal end of the elongated shaft for manipulating tissue;
   an endoscope having a tubular body including an image fiber, an endoscopic lens coupled to a distal end of the tubular body and operably coupled to the image fiber, the endoscopic lens defining a viewing field about a central axis;
   the endoscope mounted to the elongated shaft of the surgical instrument, the endoscopic lens protruding from an outer longitudinal surface of the elongated shaft, the central axis of the viewing field being oblique to the longitudinal axis of the elongated shaft and intersecting the outer longitudinal surface, the working element located within the viewing field and separated from the central axis by a distance;

wherein a portion of the central axis of the viewing field extending from the distal end of the tubular body of the endoscope in a direction towards the working element of the surgical instrument diverges from the elongated shaft and the working element of the surgical instrument without intersecting the elongated shaft or the working element of the surgical instrument; and wherein the central axis of the viewing field intersects the longitudinal axis of the elongated shaft of the surgical instrument at an intersection point that is located between the proximal and distal ends of the elongated shaft and is spaced a first distance from the distal end of the elongated shaft and wherein the endoscopic lens of the endoscope is located between the proximal and distal ends of the elongated shaft and is spaced a second distance from the distal end of the elongated shaft, the first distance being greater than the second distance.

2. The surgical apparatus of claim 1 wherein the endoscope is flexible and is mounted directly to the outer longitudinal surface of the elongated shaft of the surgical instrument.

3. The surgical apparatus of claim 1 wherein the tubular body comprises a base portion and a protruding portion oblique to the base portion, the protruding portion comprising the distal end of the tubular body and protruding from the outer longitudinal surface of the elongated shaft, the protruding portion of the tubular body extending along the central axis of the viewing field.

4. The surgical apparatus of claim 1 wherein an acute angle is formed between the central axis of the viewing field and the longitudinal axis of the elongated shaft as they extend from the intersection point in the direction towards the working element, and wherein a distance measured between the central axis of the viewing field and the surgical instrument continually increases with distance from the endoscopic lens towards the working element.

5. The surgical apparatus of claim 1 wherein the central axis of the viewing field is substantially coplanar with the longitudinal axis of the elongated shaft.

6. The surgical apparatus of claim 1 wherein the surgical instrument is a micro-surgical instrument selected from a group consisting of suctions, dissectors, and forceps.

7. The surgical apparatus of claim 1 wherein the viewing field comprises a radius, the central axis divides the viewing field into an upper hemisphere and a lower hemisphere, and the working element is visible in a portion of the lower hemisphere without being visible in the upper hemisphere, and wherein at least an inner one-third of the radius of the viewing field is free of the working element.

8. The surgical apparatus of claim 1 further comprising a coupling mechanism securing the endoscope to the elongated shaft.

9. The surgical apparatus of claim 8 wherein the coupling mechanism comprises:
a protuberance extending from the outer longitudinal surface of the elongated shaft in a first transverse direction, the protuberance located a first longitudinal distance from the distal end of the elongated shaft; and
a retaining member securing the endoscope to the elongated shaft, the retaining member located a second longitudinal distance from the distal end of the elongated shaft adjacent the protuberance, the second longitudinal distance greater than the first longitudinal distance, the retaining member exerting a force on the tubular body in a second transverse direction opposite the first transverse direction.

10. The surgical apparatus of claim 9 wherein the protuberance acts as a fulcrum on the tubular body of the endoscope that forces a portion of the endoscope to diverge from the outer longitudinal surface of the tubular body.

11. The surgical apparatus of claim 8 wherein the coupling mechanism comprises an arch structure protruding from the outer longitudinal surface of the elongated shaft, the arch structure defining a passageway for retaining a portion of the endoscope.

12. The surgical apparatus of claim 11 wherein the passageway comprises a floor that diverges from the outer longitudinal surface of the elongated shaft moving toward the distal end of the elongated shaft.

13. The surgical apparatus of claim 11 wherein the coupling mechanism further comprises:
a protuberance extending from the outer longitudinal surface of the elongated shaft, the protuberance located adjacent an exit of the passageway;
the endoscope extending through the passageway and over the protuberance, the protuberance causing the tubular body of the endo scope to diverge from the outer longitudinal surface of the elongated shaft.

14. The surgical apparatus of claim 1 wherein the elongated shaft comprises a first indexing feature and the tubular body of the endoscope comprises a second indexing feature, and wherein the first and second indexing features mate with one another so as to prevent rotation of the tubular body relative to the elongated shaft.

15. The surgical instrument of claim 1 wherein the central axis of the viewing field is oriented at an oblique angle between 5° to 45° to the longitudinal axis of the elongated shaft.

* * * * *